United States Patent
Vemulapati et al.

(10) Patent No.: US 11,262,352 B2
(45) Date of Patent: Mar. 1, 2022

(54) MAGNETIC SEPARATION OF BIOLOGICAL ENTITIES FROM FLUID SAMPLE

(71) Applicant: CORNELL UNIVERSITY, Ithaca, NY (US)

(72) Inventors: Sasank Vemulapati, Ithaca, NY (US); David Erickson, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 17/261,855

(22) PCT Filed: Jul. 22, 2019

(86) PCT No.: PCT/US2019/042887
§ 371 (c)(1),
(2) Date: Jan. 20, 2021

(87) PCT Pub. No.: WO2020/019001
PCT Pub. Date: Jan. 23, 2020

(65) Prior Publication Data
US 2021/0247390 A1    Aug. 12, 2021

Related U.S. Application Data

(60) Provisional application No. 62/701,557, filed on Jul. 20, 2018.

(51) Int. Cl.
*G01N 33/50* (2006.01)
*G01N 33/543* (2006.01)
(Continued)

(52) U.S. Cl.
CPC ..... *G01N 33/54326* (2013.01); *G01N 1/4077* (2013.01); *G01N 33/56966* (2013.01)

(58) Field of Classification Search
CPC .... B03C 1/00; B03C 1/32; B03C 1/01; B03C 1/005; G01N 33/54326; G01N 33/50; G01N 1/4077; G01N 33/56966
See application file for complete search history.

(56) References Cited

U.S. PATENT DOCUMENTS

| | | | |
|---|---|---|---|
| 4,209,259 A | 6/1980 | Rains et al. | |
| 4,710,472 A | 12/1987 | Saur et al. | |

(Continued)

FOREIGN PATENT DOCUMENTS

| | | |
|---|---|---|
| CN | 204882191 U | 12/2015 |
| CN | 103394410 B | 4/2016 |

(Continued)

OTHER PUBLICATIONS

Vemulapati et al., "H.E.R.M.E.S: Rapid Blood-Plasma Separation at the Point-of-Need," Lab Chip, 18 (21):3285-3292 (Sep. 26, 2018).

(Continued)

*Primary Examiner* — Brian J. Sines
(74) *Attorney, Agent, or Firm* — FisherBroyles, LLP; Andrew K. Gonsalves, Esq.

(57) ABSTRACT

The present disclosure relates to, inter alia, devices, systems, and methods for use in the magnetic separation of biological entities from fluid samples. This device includes a magnetic separation chamber configured to receive a fluid sample for magnetic separation, where the magnetic separation chamber includes at least two magnets mounted on the surface or in the wall of the magnetic separation chamber. The device also includes a force provider configured to move the magnetic separation chamber in a side-to-side motion to mix and/or magnetize the fluid sample. In one embodiment, the magnetic separation chamber is in a form of a sleeve and comprises a substantially central channel for loading a vessel containing the fluid sample therein. The systems and (Continued)

methods of the present disclosure involve the use of this device to separate biological entities from fluid samples.

26 Claims, 11 Drawing Sheets

(51) Int. Cl.
  *G01N 33/569* (2006.01)
  *G01N 1/40* (2006.01)

(56) References Cited

U.S. PATENT DOCUMENTS

| | | | |
|---|---|---|---|
| 4,812,401 | A | 3/1989 | Tarnowski et al. |
| 5,466,574 | A | 11/1995 | Liberti et al. |
| 5,681,478 | A | 10/1997 | Lea et al. |
| 5,876,593 | A | 3/1999 | Liberti et al. |
| 6,136,182 | A | 10/2000 | Dolan et al. |
| 6,689,615 | B1 | 2/2004 | Murto et al. |
| 6,884,357 | B2 | 4/2005 | Siddiqi |
| 8,137,903 | B2 | 3/2012 | Kaufman et al. |
| 9,353,410 | B2 | 5/2016 | Li et al. |
| 2003/0170686 | A1 | 9/2003 | Hoet et al. |
| 2003/0203507 | A1 | 10/2003 | Liberti et al. |
| 2006/0081539 | A1 | 4/2006 | Safar et al. |
| 2006/0252054 | A1 | 11/2006 | Lin et al. |
| 2010/0018125 | A1 | 1/2010 | Oh |
| 2010/0203578 | A1 | 8/2010 | Geiger et al. |
| 2010/0227387 | A1 | 9/2010 | Safar et al. |
| 2010/0264090 | A1 | 10/2010 | Ellis et al. |
| 2011/0212432 | A1 | 9/2011 | Torgersen et al. |
| 2013/0122485 | A1 | 5/2013 | Hong |
| 2015/0031037 | A1 | 1/2015 | Li et al. |
| 2015/0185234 | A1 | 7/2015 | Gibbons et al. |
| 2015/0204843 | A1 | 7/2015 | Wende et al. |
| 2016/0103045 | A1 | 4/2016 | Scott et al. |
| 2017/0073667 | A1* | 3/2017 | Ohashi ............... C12N 15/1013 |
| 2017/0266653 | A1 | 9/2017 | Pollack et al. |
| 2018/0292394 | A1 | 10/2018 | Soldo |

FOREIGN PATENT DOCUMENTS

| | | |
|---|---|---|
| EP | 1311820 B1 | 2/2015 |
| WO | 2001049419 A1 | 7/2001 |
| WO | 2017196798 A1 | 11/2017 |

OTHER PUBLICATIONS

International Searching Authority (WO/ISA), International Search Report and Written Opinion issued in PCT/US2019/042887, dated Oct. 4, 2019.

Kim et al., "Low-Cost, Disposable Microfluidics Device for Blood Plasma Extraction Using Continuously Alternating Paramagnetic and Diamagnetic Capture Modes," Biomicrofluidics, 10:024110, pp. 1-17 (2016).

Khashan et al., "Microdevice for Continuous Flow Magnetic Separation for Bioengineering Applications," J. Micromech. Microeng., 27:055016, pp. 1-10 (2017).

Chen et al., "Three-Dimensional Modeling of a Portable Medical Device for Magnetic Separation of Particles from Biological Fluids," Phys. Med. Biol., 52:5205-5218 (2007).

* cited by examiner

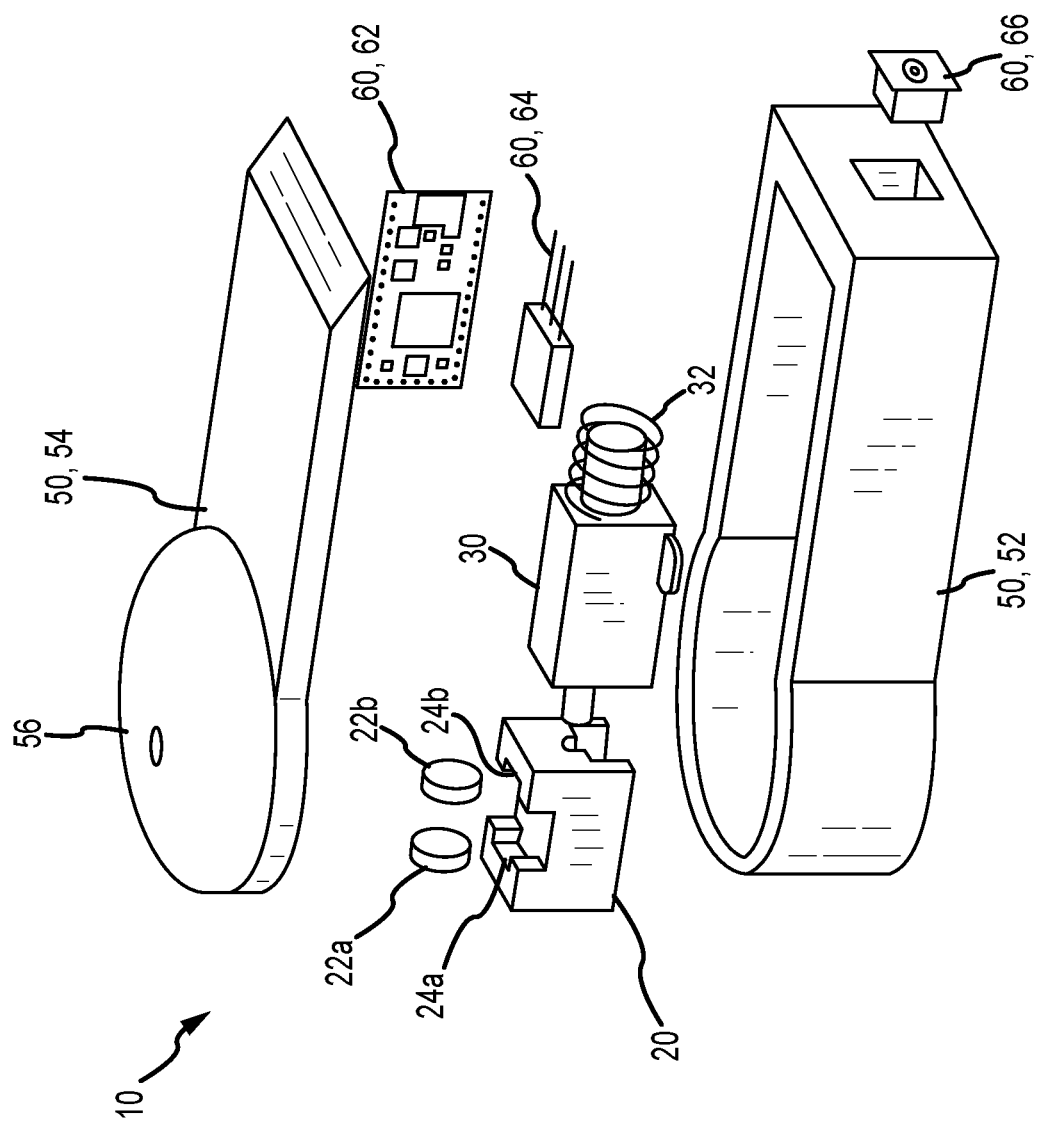

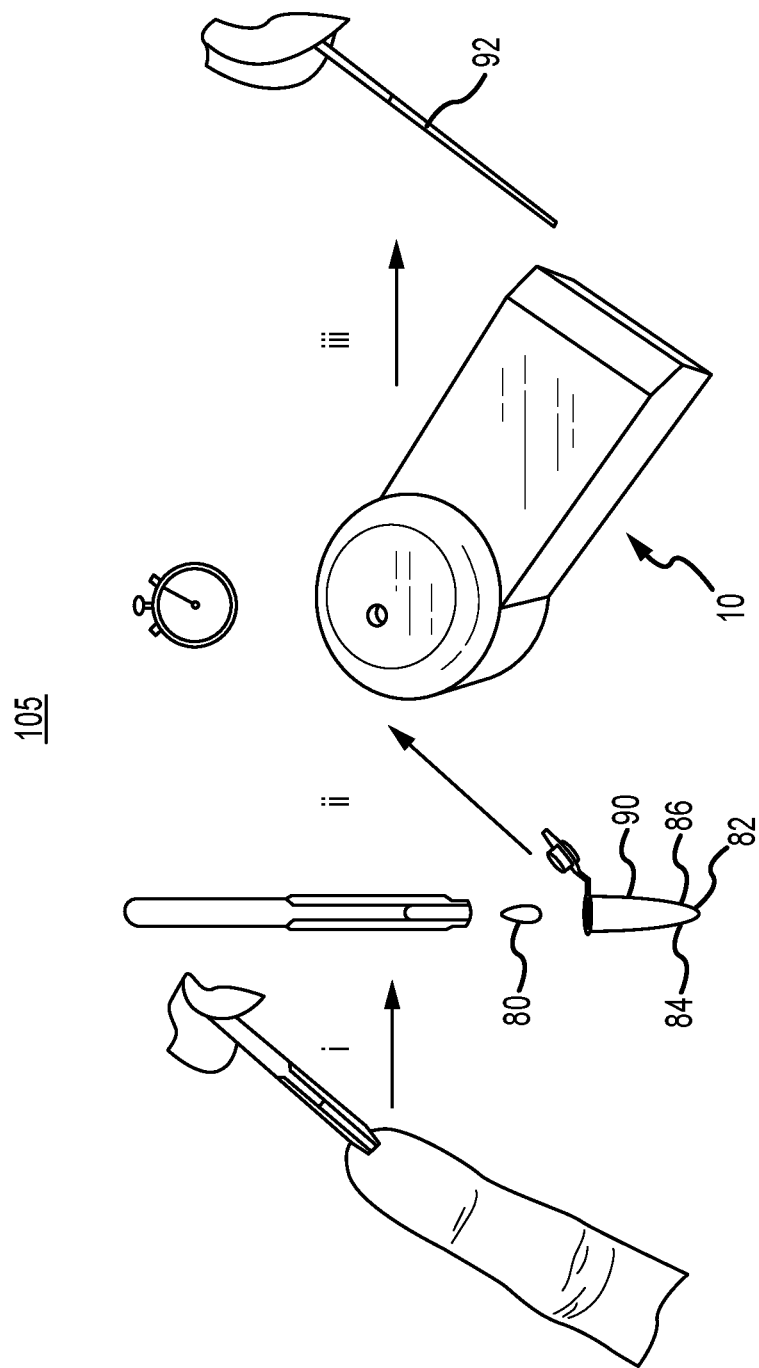

MAGNETIC SEPARATION OF BIOLOGICAL ENTITIES FROM FLUID SAMPLE

CROSS-REFERENCE TO RELATED APPLICATIONS

This application is a U.S. National Phase filing under 35 U.S.C. § 371 of International Application No. PCT/US2019/042887, filed Jul. 22, 2019, and published as WO 2020/019001 A1 on Jan. 23, 2020, which claims priority benefit of U.S. Provisional Patent Application Ser. No. 62/701,557, filed Jul. 20, 2018, the disclosures of which are hereby incorporated by reference herein in their entirety.

STATEMENT REGARDING FEDERALLY SPONSORED RESEARCH

This invention was made with Government support under Grant Number 1343058 awarded by the National Science Foundation. The Government has certain rights in the invention.

FIELD OF THE INVENTION

The present disclosure relates to, inter alia, devices, systems, and methods relating to the magnetic separation of biological entities from fluid samples.

BACKGROUND OF THE INVENTION

The US blood testing market is estimated at $20 billion and is expected to increase to $30 billion by 2030 (1). This predicted growth stems from an increasing demand for CLIA-waived testing environments, such as Urgent Care and Minute Clinics, that offer diagnostic capabilities at lower costs and greater convenience than conventional laboratory testing. CLIA-waived clinics embody a shift in the healthcare landscape towards decentralization and higher accessibility of medical testing. The separation of unwanted cellular material is critical for the accuracy and reliability of many molecular diagnostics tools (2), for example many blood tests require that plasma is separated from red blood cells prior to analysis. In commercial blood testing laboratories, centrifuges are almost exclusively employed to perform separation and is a key first step to facilitate accurate quantitative diagnostics (3). However, the US Food and Drug Administration (FDA) classifies centrifuges as 'moderately' complex devices that are unsuitable for use in CLIA-waived environments (4). This constraint has bottlenecked the translational ability of diagnostic technologies as centrifuges are unable to adapt for use at the point-of-need and are becoming increasingly obsolete in a landscape that is seeking the further decentralization of testing services.

Passive filtration membranes are a solution to perform cell separation at the point-of-need and are often used with lateral flow assays (5). Enabled by capillary action, the membranes operate on the principle of selectively preventing particles of a certain size from flowing through them. While inexpensive and easy to manufacture, the performance of these membranes is marred by inconsistencies in separation caused by clogged pores. Inconsistencies manifest themselves as variability in amount of plasma that is obtained during each run which deters the performance of quantitative lateral flow tests. Immunochemistry is sensitive to a variation in amount of sample that is used for analysis (6,7). Additionally, the recovery rates of these methods are low (8) (less than 30% of available plasma) which presents a barrier for analysis of analytes at low concentrations and sizes (9).

Several microfluidic approaches have been demonstrated in literature that achieve high levels of separation. These methods can be broadly classified into "active" and "passive" techniques (10). Active techniques employ an external field (acoustic, electric or magnetic) that is used to align or immobilize the blood cells so as to enable the plasma to be separated in a continuous flow format. Passive methods typically separate the cells using hydrodynamic effects or separating pillars using cleverly designed and intricate microfluidic fabrication architecture (11-13). While these techniques have been excellent demonstrative proof-of-concepts, they lack the ability to be commercialized as microfluidic fabrication is a highly involved and expensive process that lacks scalability (14). Further, in the case of active methods, the complex designs are often too cost-ineffective to integrate into existing microfluidic methods rendering them impractical for use at the point-of-need (9). To address the high cost and lack of accessibility, many researchers have used common household items and toys like salad spinners and egg beaters to achieve plasma separation (15-17). These designs were cleverly engineered to simulate centrifugation but are not robust enough to operate in point-of-need clinical settings. There is a need for low-cost technologies that can offer highly efficient blood-plasma separation at the point-of-need with high reliability and efficiency. A 'simple' method would further enable present day diagnostics to transition for use at the point-of-need (18-21) and enable the decentralization of blood testing services.

The present invention is directed to overcoming these and other deficiencies in the art.

SUMMARY OF THE INVENTION

The present disclosure relates to, inter alia, devices, systems, and methods for use in the magnetic separation of biological entities from fluid samples.

In one aspect, the present disclosure provides a device for use in magnetic separation of a target biological entity from a fluid sample. The device includes: (a) a magnetic separation chamber configured to receive a fluid sample for magnetic separation, wherein said magnetic separation chamber comprises two magnets mounted on opposing sidewalls a sufficient distance from one another so as to prevent interference between the magnetic field of each magnet, and wherein the magnetic separation chamber is configured to receive and maintain the fluid sample at a position between the two magnets during operation of the device; and (b) an actuator functionally coupled to the magnetic separation chamber, wherein said actuator comprises a linear actuator configured to move the magnetic separation chamber laterally in a side-to-side motion so as to keep the two magnets in line with the fluid sample during operation of the actuator.

In another aspect, the present disclosure provides a system for use in magnetic separation of a target biological entity from a fluid sample. This system includes: (a) at least one device according to the present disclosure; and (b) a plurality of magnetic beads each functionalized to bind to the target biological entity, thereby being effective to capture and separate the target biological entity from the fluid sample.

In another aspect, the present disclosure provides a method for separating a target biological entity from a fluid sample. This method involves the steps of: (a), said method comprising the steps of: (a) providing a device according to the present disclosure; (b) combining the fluid sample with a plurality of magnetic beads functionalized to bind to the target biological entity, wherein the combining is performed in a vessel comprising a tube or other suitable container for containing the fluid sample during operation of the device; (c) positioning the vessel containing the fluid sample and the functionalized magnetic beads between the two magnets of the magnetic separation chamber of the device; and (d) operating the device in a manner sufficient to capture the target biological entity on the functionalized magnetic beads, thereby yielding a supernatant free of or substantially free of said target biological entity.

In another aspect, the present disclosure is directed to a device for use in magnetic separation of a target biological entity from a fluid sample. This device includes: (a) a magnetic separation chamber configured to receive a fluid sample for magnetic separation, wherein said magnetic separation chamber comprises at least two magnets mounted on the surface or in the wall of the magnetic separation chamber; and (b) a force provider configured to move the magnetic separation chamber in a side-to-side motion to mix and/or magnetize the fluid sample. In one embodiment, the magnetic separation chamber is in a form of a sleeve and comprises a substantially central channel for loading a vessel containing the fluid sample therein, and further includes at least two side channels each containing at least one magnet therein. In certain embodiments, the side channels are positioned at opposite ends and opposite sides of the substantially central channel.

In another aspect, the present disclosure is directed to a method for separating a target biological entity from a fluid sample. The method involves the steps of: (a) providing a device according to the present disclosure; (b) combining the fluid sample with a plurality of magnetic beads functionalized to bind to the target biological entity, wherein the combining is performed in a vessel comprising a tube or other suitable container for containing the fluid sample during operation of the device; (c) positioning the vessel containing the fluid sample and the functionalized magnetic beads between the two magnets of the magnetic separation chamber of the device; and (d) operating the device in a manner sufficient to capture the target biological entity on the functionalized magnetic beads, thereby yielding a supernatant free of or substantially free of said target biological entity. In one embodiment, the magnetic separation chamber is in a form of a sleeve and comprises a substantially central channel for loading a vessel containing the fluid sample therein, and further includes at least two side channels each containing at least one magnet therein. In certain embodiments, the side channels are positioned at opposite ends and opposite sides of the substantially central channel.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, if provided, like reference numerals contained in the drawings are meant to identify similar or identical elements.

FIGS. 1A-1D are schematic drawings of different view of one embodiment of a device of the present disclosure. FIG. 1A is an exploded view of the device. FIG. 1B is a perspective view of the device. FIG. 1C is a top view of the device. FIG. 1D is a side view of the device.

FIG. 2 is a schematic of one embodiment of a system of the present disclosure, which also illustrates a method of using the system.

FIG. 4A illustrates the use of the portable benchtop H.E.R.M.E.S device and system in accordance with a method of the present disclosure. As shown in FIG. 4A, in one embodiment, the method involves three simple steps: (i) collect and load the sample in a test tube precoated with functionalized magnetic beads, (ii) place sample in H.E.R.M.E.S and wait for 90 seconds, and (iii) remove sample and extract plasma using a capillary tube. FIG. 4B illustrates a size comparison of the portable benchtop H.E.R.M.E.S device against a standard laboratory centrifuge (Fisherbrand accuSpin Micro 17). FIG. 4C illustrates a side and top profile view of a portable benchtop device of the present disclosure. FIG. 4D illustrates an exploded view of a portable benchtop H.E.R.M.E.S device of the present disclosure, showing its internal components.

FIG. 5A illustrates the effect of aggregation of blood cells prior to capture. FIG. 5B illustrates separation of plasma from captured red blood cells with application of a magnetic field in accordance with the present disclosure, as seen under a microscope.

FIG. 7A is a graph of a plot showing the effect of the aggregation agent on performance of H.E.R.M.E.S. Three different sample volumes were used as noted in the legend. A non-linear relationship is observed between the amount of blood cells and the amount of aggregation agent required to capture them. An average of 34 µL and 53 µL of total recovered plasma were obtained in the cases of samples tested using 80 and 120 µL volumes. Standard deviation for each sample is indicated with error bars. (n=2). The inset shows that the concentration of magnetic beads does not affect the performance significantly. FIG. 7B are images of separated plasma at three different aggregation agent concentrations. From this figure it is clear that a concentration of around 3.5 µg/mL is optimal to obtain highly pure plasma.

FIG. 8A is a graph of a plot comparing the performance of plasma obtained from H.E.R.M.E.S and commercially available filtration paper. A starting volume of 40 µL was used for each test and 15 µL of plasma was used for the strips that were used with H.E.R.M.E.S. The pictures on the left and right side of the plot are images of test strips run using plasma obtained from H.E.R.M.E.S and filtration paper respectively. In general, one can note a higher T/C ratio for all the samples that used H.E.R.M.E.S for separation. Further, one can observe a higher coefficient of determination $R^2$ and a sharper slope in the case of samples processed with H.E.R.M.E.S. The standard deviation of each sample (n=2) is indicated by error bars. FIG. 8B is a graph illustrating a comparison of the mean coefficient of variations (CV=standard deviation/ mean*100) between the two types of plasma. The CV of all samples from H.E.R.M.E.S was lower than 10%. FIG. 8C is a graph illustrating a comparison of the ROC curves (generated using the Delong method). The a.u.c from samples purified by H.E.R.M.E.S was 1 and the a.u.c from filtered samples was 0.789.

FIG. 9A illustrates an external view of the sleeve. FIG. 9B illustrates an internal cross-sectional view of the sleeve.

DESCRIPTION OF THE INVENTION

Figure 1B:
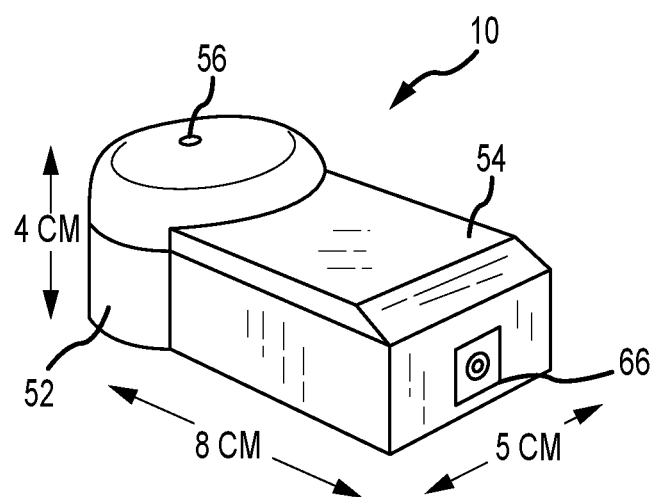
Figure 1C:
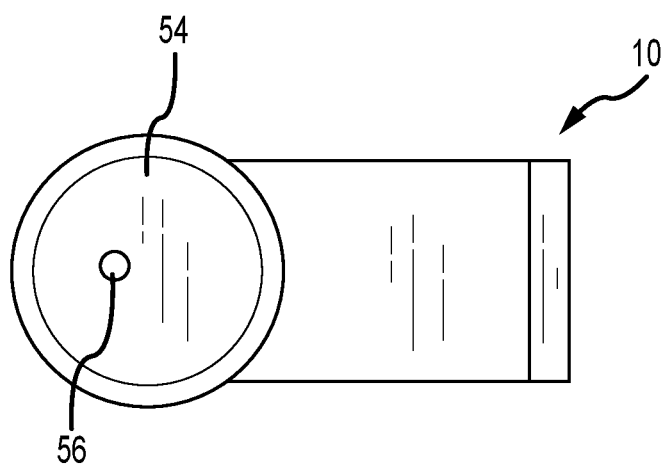

Disclosed herein are, inter alia, devices, systems, and methods relating to the magnetic separation of biological entities from fluid samples.

Device for Use in Magnetic Separation of a Target Biological Entity from a Fluid Sample In one aspect, the present disclosure is directed to a device for use in magnetic separation of a target biological entity from a fluid sample. The device includes: (a) a magnetic separation chamber configured to receive a fluid sample for magnetic separation, wherein said magnetic separation chamber comprises two magnets mounted on opposing sidewalls a sufficient distance from one another so as to prevent interference between the magnetic field of each magnet, and wherein the magnetic separation chamber is configured to receive and maintain the fluid sample at a position between the two magnets during operation of the device; and (b) an actuator functionally coupled to the magnetic separation chamber, wherein said actuator comprises a linear actuator configured to move the magnetic separation chamber laterally in a side-to-side motion so as to keep the two magnets in line with the fluid sample during operation of the actuator.

In one embodiment, the magnetic separation chamber is configured to receive a fluid sample having a volume of up to 200 microliters.

In one embodiment, the magnetic separation chamber is configured to receive a vessel comprising a tube or other suitable container containing the fluid sample.

In one embodiment, the magnets are circular magnets.

In one embodiment, the magnets are neodymium magnets.

In one embodiment, the actuator is an actuating solenoid. A suitable actuating solenoid for use in the present disclosure can include, without limitation, a linear actuator solenoid.

In one embodiment, the actuating solenoid is a 12 volt actuating solenoid.

In one embodiment, the device further includes a housing unit configured to house the magnetic separation chamber and the actuator.

In one embodiment, the housing unit comprises a base portion and a top cover portion, wherein the base portion is configured to hold the magnetic separation chamber and the actuator, and wherein the top cover portion is configured to fit over and cover the base portion and its contents.

In one embodiment, the top cover portion further comprises an opening for inserting the fluid sample into a position between the two magnets of the magnetic separation chamber.

In one embodiment, the housing unit is configured to further house onboard electronics components effective to operate the actuator and to enable automation of the device.

In one embodiment, the onboard electronics components comprise at least one component selected from the group consisting of a microcontroller, a transistor, and a power input jack.

In one embodiment, the power input jack is suitable for use with a standard 12 volt, 0.5 ampere wall power supply. In other embodiments, the device of the present disclosure can be battery powered.

In one embodiment, the device is in a form of a portable benchtop device.

The device according to claim 14, wherein the portable benchtop device has dimensions not greater than 4 centimeters in height, 5 centimeters in width, and 8 centimeters in length.

In one embodiment, the device is in a form suitable for use for point-of-need diagnostics of the fluid sample.

Turning to FIGS. 1A-1D, there is illustrated one embodiment of device 10 of the present disclosure. As shown, device 10 can be used for magnetic separation of a target biological entity from a fluid sample. In certain embodiments, device 10 includes magnetic separation chamber 20 configured to receive a fluid sample for magnetic separation. As shown in FIG. 1A, magnetic separation chamber 20 includes two magnets (22a, 22b) mounted on opposing sidewalls (24a, 24b) a sufficient distance from one another so as to prevent interference between the magnetic field of each magnet (22a, 22b). Magnetic separation chamber 20 is configured to receive and maintain the fluid sample at a position between the two magnets (22a, 22b) during operation of device 10. Device 10 also includes actuator 30 functionally coupled to magnetic separation chamber 20, where actuator 30 includes linear actuator 32 configured to move the magnetic separation chamber 20 laterally in a side-to-side motion so as to keep the two magnets (22a, 22b) in line with the fluid sample during operation of actuator 30.

Figure 1D:
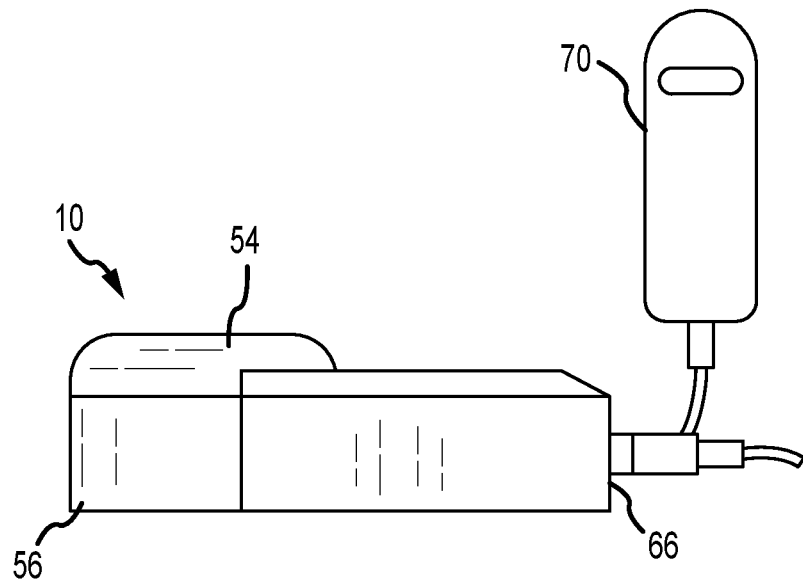

As shown in FIGS. 1A-1D, in certain embodiments, device 10 further includes housing unit 50 configured to house magnetic separation chamber 20 and actuator 30. In certain embodiments, housing unit 50 includes base portion 52 and top cover portion 54. Base portion 52 can be configured to hold magnetic separation chamber 20 and actuator 30, where top cover portion 54 is configured to fit over and cover base portion 52 and its contents (e.g., magnetic separation chamber 20, actuator 30 with linear actuator 32, microcontroller 62, transistor 64, and power input jack 66). As shown, top cover portion 54 can further include opening 56 for inserting the fluid sample into a position between the two magnets (22a, 22b) of magnetic separation chamber 20. In one embodiment, housing unit 50 is configured to further house onboard electronics components 60 effective to operate actuator 30 and to enable automation of device 10. In one embodiment, onboard electronics components 60 can include, without limitation, at least one component selected from microcontroller 62, transistor 64, and/or power input jack 66. As shown in FIG. 1D, in certain embodiments, power input jack 66 is suitable for use with a standard 12 volt, 0.5 ampere wall power supply 70.

As shown in FIG. 1B, in one embodiment, device 10 is in a form of a portable benchtop device. Without intending to limit the scope of the described device, as illustrated in FIG. 1B, in a particular embodiment, portable benchtop device 10 can have dimensions not greater than 4 centimeters in height, 5 centimeters in width, and 8 centimeters in length. Such dimensions are particularly suitable for use for point-of-need diagnostics of fluid samples.

System for Use in Magnetic Separation of a Target Biological Entity from a Fluid Sample In another aspect, the present disclosure is directed to a system for use in magnetic separation of a target biological entity from a fluid sample. This system includes: (a) at least one device according to the present disclosure; and (b) a plurality of magnetic beads each functionalized to bind to the target biological entity, thereby being effective to capture and separate the target biological entity from the fluid sample.

In one embodiment, the system further includes an aggregation agent configured to group together an aggregate of a plurality of the target biological entities prior to the capture and separation of the target biological entity from the fluid sample.

In one embodiment, the aggregation agent is selected from the group consisting of an antibody, a protein, dextran, polyvinylpyrollidone, polyoxyethylene, fibrinogen, immunoglobulin IgM and IgG, calcium chloride, and combinations thereof.

In one embodiment, the target biological entity are red blood cells and the aggregation agent is an antibody that binds to red blood cells non-specifically, irrespective of blood type.

In one embodiment, the aggregation agent is an antibody that binds to a surface marker of red blood cells.

In one embodiment, the surface marker of the red blood cell is selected from the group consisting of CD235a and TER119.

In one embodiment, the plurality of magnetic beads and the aggregation agent are contained in a vessel comprising a tube or other suitable container for containing the fluid sample during operation of the device.

In one embodiment, the plurality of magnetic beads and the aggregation agent are provided together in a storage buffer.

In one embodiment, the plurality of magnetic beads are conjugated to the aggregation agent prior to adding the fluid sample.

In one embodiment, the plurality of magnetic beads and the aggregation agent are dried directly in a collection container prior to adding the fluid sample.

In one embodiment, the collection container is a vessel comprising a tube or other suitable container for containing the fluid sample during operation of the device.

In one embodiment, the target biological entity is selected from the group consisting of white blood cells, contaminants, waste products, and excess reagents contained in the fluid sample.

In one embodiment, the system further includes a collection component for collecting a supernatant produced after capture and separation of the target biological entity from the fluid sample.

In one embodiment, the collection component is a capillary tube configured to passively uptake the supernatant.

In one embodiment, the fluid sample is a blood sample, the target biological entity comprises red blood cells, and the supernatant comprises plasma.

Turning to FIG. 2, there is illustrated one embodiment of how device 10 and system 105 can be used in a method of magnetic separation of target biological entities 84 from fluid sample 80 in accordance with the present disclosure. As shown in FIG. 2, in one embodiment, system 105 includes at least one device 10 according to the present disclosure and a plurality of magnetic beads 82 each functionalized to bind to target biological entity 84, thereby being effective to capture and separate target biological entity 84 from fluid sample 80. As shown in FIG. 2, in one embodiment, the plurality of magnetic beads 82 and aggregation agent 86 are contained in vessel 90, where vessel 90 can be a tube or other suitable container for containing fluid sample 80 during operation of device 10. In one embodiment, system 105 further includes collection component 92 for collecting a supernatant produced after capture and separation of target biological entity 84 from fluid sample 80. As shown in FIG. 2, in one embodiment, collection component 92 is a capillary tube configured to passively uptake the supernatant.

Method for Use in Magnetic Separation of a Target Biological Entity from a Fluid Sample In another aspect, the present disclosure is directed to a method for separating a target biological entity from a fluid sample. This method involves the steps of: (a) providing a device according to the present disclosure; (b) combining the fluid sample with a plurality of magnetic beads functionalized to bind to the target biological entity, wherein the combining is performed in a vessel comprising a tube or other suitable container for containing the fluid sample during operation of the device; (c) positioning the vessel containing the fluid sample and the functionalized magnetic beads between the two magnets of the magnetic separation chamber of the device; and (d) operating the device in a manner sufficient to capture the target biological entity on the functionalized magnetic beads, thereby yielding a supernatant free of or substantially free of said target biological entity.

In one embodiment, the operating step comprises running the actuator to enable the magnetic separation chamber to function to capture the target biological entity with the functionalized magnetic beads and concentrate them proximate to just one of the two magnets, thereby separating the target biological entity from the fluid sample.

In one embodiment, running the actuator comprises moving the magnetic separation chamber laterally in a side-to-side motion with respect to the fluid sample for a sufficient number of strokes to homogenously distribute the functionalized magnetic beads among the target biological entity and concentrate them proximate to just one of the two magnets, thereby separating the target biological entity from the fluid sample.

In one embodiment, the number of strokes is not greater than 100 strokes, not greater than 50 strokes, not greater than 40 strokes, not greater than 30 strokes, not greater than 20 strokes, or not greater than 10 strokes.

In one embodiment, the sufficient number of strokes is completed within not more than 180 seconds, not more than 150 seconds, not more than 120 seconds, not more than 90 seconds, not more than 60 seconds, or not more than 30 seconds.

In one embodiment, the method further involves collecting the supernatant from the vessel.

In one embodiment, the collecting is performed using a capillary tube.

In one embodiment, the method further involves collecting and analyzing the supernatant and/or the captured target biological entity using one or more diagnostic tool or technique of interest. Suitable diagnostic tools and techniques of interest are well known in the art and contemplated for use with the devices, systems, and methods of the present disclosure.

In one embodiment, the method does not involve a centrifugation step to separate the target biological entity from the fluid sample.

In one embodiment, the magnetic beads are conjugated to an aggregation agent prior to the combining step, and wherein said aggregation agent is configured to group together an aggregate of a plurality of the target biological entities prior to the capture and separation of the target biological entity from the fluid sample.

In one embodiment, the aggregation agent is selected from the group consisting of an antibody, a protein, dextran, polyvinylpyrollidone, polyoxyethylene, fibrinogen, immunoglobulin IgM and IgG, calcium chloride, and combinations thereof.

In one embodiment, the target biological entity are red blood cells and the aggregation agent is an antibody that binds to red blood cells non-specifically, irrespective of blood type.

In one embodiment, the aggregation agent is an antibody that binds to a surface marker of red blood cells.

In one embodiment, the surface marker of the red blood cell is selected from the group consisting of CD235a and TER119.

In one embodiment, the plurality of magnetic beads and the aggregation agent are contained in a vessel comprising a tube or other suitable container for containing the fluid sample during operation of the device.

In one embodiment, the plurality of magnetic beads and the aggregation agent are provided together in a storage buffer.

In one embodiment, the plurality of magnetic beads are conjugated to the aggregation agent prior to adding the fluid sample.

In one embodiment, the plurality of magnetic beads and the aggregation agent are dried directly in a collection container prior to adding the fluid sample.

In one embodiment, the collection container is a vessel comprising a tube or other suitable container for containing the fluid sample during operation of the device.

In one embodiment, the target biological entity is selected from the group consisting of white blood cells, contaminants, waste products, and excess reagents contained in the fluid sample.

In one embodiment, the method further involves using a collection component for collecting a supernatant produced after capture and separation of the target biological entity from the fluid sample.

In one embodiment, the collection component is a capillary tube configured to passively uptake the supernatant.

In one embodiment, the fluid sample is a blood sample, the target biological entity comprises red blood cells, and the supernatant comprises plasma.

Figure 3:
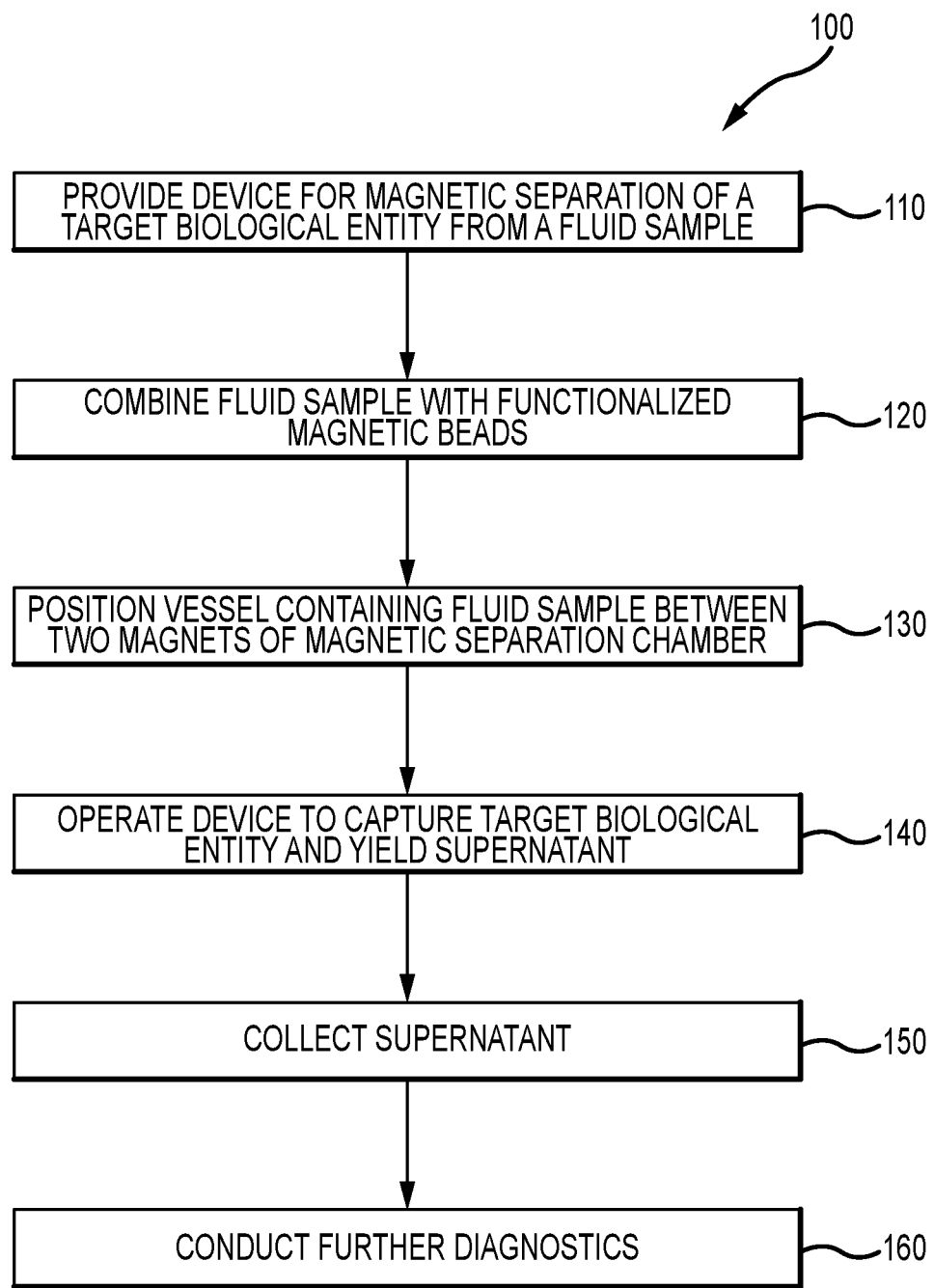
FIG. 3 is a flow chart of one embodiment of a method of magnetic separation of biological entities from a fluid sample in accordance with the present disclosure.

Turning to FIG. 3, there is illustrated one embodiment of a method for separating a target biological entity from a fluid sample. As shown in the flow chart of FIG. 3, separation method 100 involves: (a) step 110: providing a device according to the present disclosure; (b) step 120: combining the fluid sample with a plurality of magnetic beads functionalized to bind to the target biological entity, wherein the combining is performed in a vessel comprising a tube or other suitable container for containing the fluid sample during operation of the device; (c) step 130: positioning the vessel containing the fluid sample and the functionalized magnetic beads between the two magnets of the magnetic separation chamber of the device; and (d) step 140: operating the device in a manner sufficient to capture the target biological entity on the functionalized magnetic beads, thereby yielding a supernatant free of or substantially free of said target biological entity. In one embodiment, method 100 further involves step 150: collecting the supernatant from the vessel. In one embodiment, method 100 further involves step 160: collecting and analyzing the supernatant and/or the captured target biological entity using one or more diagnostic tool or technique of interest.

Further Attributes of the Disclosed Device, System, and Method of Magnetic Separation As provided herein, in various aspects, the devices, systems, and methods of magnetic separation of as various attributes and characteristics over the existing art. In a particular embodiment, the aggregation agent is effective to aggregate the biological entity within the sample and the magnetic separation means is effective to mix, capture, and isolate the aggregated biological entity from the sample.

In one embodiment, the magnetic separation means can include a pair of magnets configured to generate a mixing effect within the sample.

In one embodiment, the system can further include magnetic beads conjugated to the aggregation agent.

In one embodiment, the magnetic separation means can include a pair of magnets configured to homogenously distribute the magnetic beads/aggregation agent among the biological entity.

In one embodiment, the sample is blood. However, the sample can be any biological sample from any biological source.

In one embodiment, the biological entity can include, without limitation, red blood cells, white blood cells, contaminants, waste products, excess reagents, and the like. However, the biological entity can include any entity of interest that is contained in the sample.

In one embodiment, the system used in the method includes an aggregation agent and a magnetic separation means.

In one embodiment, the aggregation agent used in the method is effective to aggregate the biological entity within the sample and the magnetic separation means is effective to mix, capture, and isolate the aggregated biological entity from the sample.

In one embodiment, the magnetic separation means used in the method can include, without limitation, a pair of magnets configured to generate a mixing effect within the sample.

In one embodiment, magnetic beads are conjugated to the aggregation agent used in the method.

In one embodiment, the magnetic separation means used in the method can include, without limitation, a pair of magnets configured to homogenously distribute the magnetic beads/aggregation agent among the biological entity.

In one embodiment, the system used in the method can further include a capillary collection component, with the capillary collection component being used to collect the isolated biological entity. In a particular embodiment, the capillary collection component is a capillary tube.

In one aspect the present disclosure involves the use of functionalized magnetic beads in combination with a stable aggregation agent to capture and separate biological entities of interest (e.g., blood cells, fat cells) from a fluid sample using an external magnetic field. The purified sample can be extracted using a capillary tube.

In one aspect, the present disclosure provides a system referred to herein as High Efficiency Rapid Magnetic Erythrocyte Separator (abbreviated herein as H.E.R.M.E.S or HERMES), a portable low-cost system that enables the separation and extraction of red blood cells from plasma within a short period of time (e.g., within 2 minutes). Broadly speaking, HERMES can perform highly efficient separation of biological agents from a biological sample. With the aggregation agent, this system and associated method are particularly useful for capturing biological entities that are present in large concentrations with respect to other entities in the sample. For example, the system and method can be used in situations that require the removal of contaminants, waste products or excess reagents in a biological sample.

Provided below are illustrative examples of various components, aspects, and embodiments of the HERMES system and associated methods.

Aggregation agent—In certain embodiments, HERMES uses a stable aggregation agent to clump red blood cells together thereby reducing the number of effective targets that need to be captured. Calculations show that a 2000-fold increase in efficiency is noticed when the aggregation agent is added. Note that the blood cells have been used just as an example. The aggregation agent can be used for any biological agent of interest.

In one embodiment, the aggregation agent can be an antibody that binds to red blood cells non-specifically. As understood in the art, antibodies for blood cells generally refer to antibodies specific to antigens present on the surface of the red blood cell. Thus, when determining the blood type of a person, i.e., type A, type B, type AB, and type 0, references to A and B are specific antigens while type 0 simply refers to "having no antigen."

In one embodiment, the aggregation agent can be an antibody that binds non-specifically to every red blood cell irrespective of blood type (one source being Rockland antibodies). Thus, it is not necessary to know what the antibody binds to on the surface of the cell. In certain embodiments, the antibody can bind to a marker known as CD235a which is known to be expressed on the surface of all mature red blood cells. There are other known cell markers like TER119 and so on. In a particular embodiment, the aggregation agent is a protein that is capable of non-specifically binding to the surface markers of red blood cells (or the entity that needs to be captured). Other suitable aggregation agents can include, without limitation, dextran, polyvinylpyrrolidone, polyoxyethylene, fibrinogen, immunoglobulin IgM and IgG, calcium chloride, and the like.

Contact free mixing—In certain embodiments, HERMES uses a pair of magnets that are moved in a particular direction with respect to the sample in order to homogenously distribute the beads amongst the blood cells. Efficient mixing enables highly efficient capture. This also removes the need for other lab equipment like pipetting devices, vortex mixers etc. In a particular case, a linear actuator is used to manipulate the sample in one direction hereby simplifying the capture process as we can use the same magnetic field for capture. For example, the two magnetic fields are placed far enough away from each other so as to not cause an interference with each other.

Dry stored reagents—In certain embodiments, the beads and aggregation agent are dried directly in the tube so there is no dilution that takes place due to addition of liquid reagents. This means that the resulting plasma can be used directly in an immunoassay or similar form of diagnostic test without the need for additional processing. Note that plasma is used in this specific example but whatever resulting fluid remains from separation can be appropriately substituted in this claim as well.

No washing step—In certain embodiments, since the objective is only in obtaining erythrocyte depleted plasma there is no need for a washing step to get rid of excess reagents.

Capillary collection—In certain embodiments, once the plasma is separated it is collected using a capillary tube that can passively uptake the plasma once it is dipped. This feeds in to the previous claim of not needing lab equipment such as pipettes.

Single Vessel—In certain embodiments, HERMES uses a single vessel to perform sample collection, capture, separation and extraction. The sample is not moved from the vessel until extraction.

Other Applications for HERMES:

Various embodiments of the HERMES system and associated methods can be used in a wide variety of applications involving the separation of biological agents from a biological sample. Below are some specific illustrative examples of other applications of the HERMES system and methods.

White blood cell isolation—In certain embodiments, HERMES can be used as a technology that isolates white blood cells instead of a technology that removes red blood cells. White blood cells contain DNA that can be used for genetic testing. In some cases, they can also contain DNA of infectious agents. In this situation, one could use Polymerase Chain Reaction methods to amplify the DNA and analyze it.

Hematocrit Determination—In certain embodiments, once the red blood cells are isolated using HERMES, one can use image capture and analysis to quantify the amount of red blood cells present in the sample thereby giving a value for hematocrit, which is a useful check for anemia or a complete blood count.

Aspects of one embodiment of the present invention are described in more detail in Example 1, which details the design and principle of the High Efficiency Rapid Magnetic Erythrocyte Separator (H.E.R.M.E.S), a portable low-cost system that enables the separation and extraction of red blood cells from plasma within 2 minutes. H.E.R.M.E.S uses functionalized magnetic beads to capture and separate red blood cells and achieves near perfect separation, rivaling the efficiency of that of a commercial centrifuge while using inexpensive raw materials. H.E.R.M.E.S employs a stand-alone protocol that does not require the use of any specialized lab equipment such as pipettes. As shown in Example 1, the efficacy of H.E.R.M.E.S is demonstrated with the help of human samples, and further proves that H.E.R.M.E.S improves the performance of existing lateral flow assays in comparison to commercially available filtration membranes.

Sleeve Device and Use Thereof in Magnetic Separation

Figure 9A:
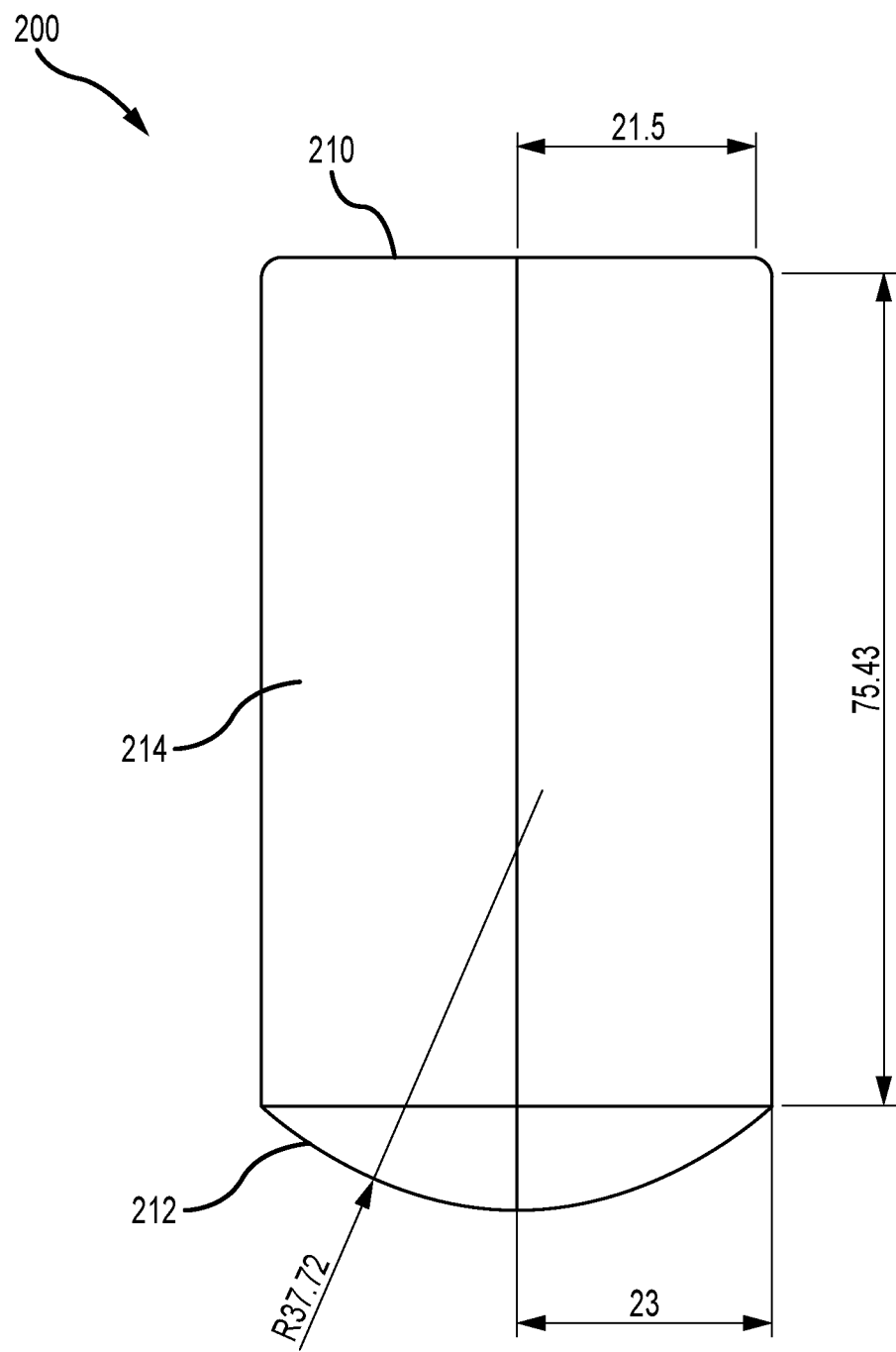
FIGS. 9A-9B are schematic drawings of one embodiment of a magnetic separation chamber in the form of a sleeve for use in magnetic separation of a biological entity from a fluid sample according to the present disclosure.
Figure 9B:
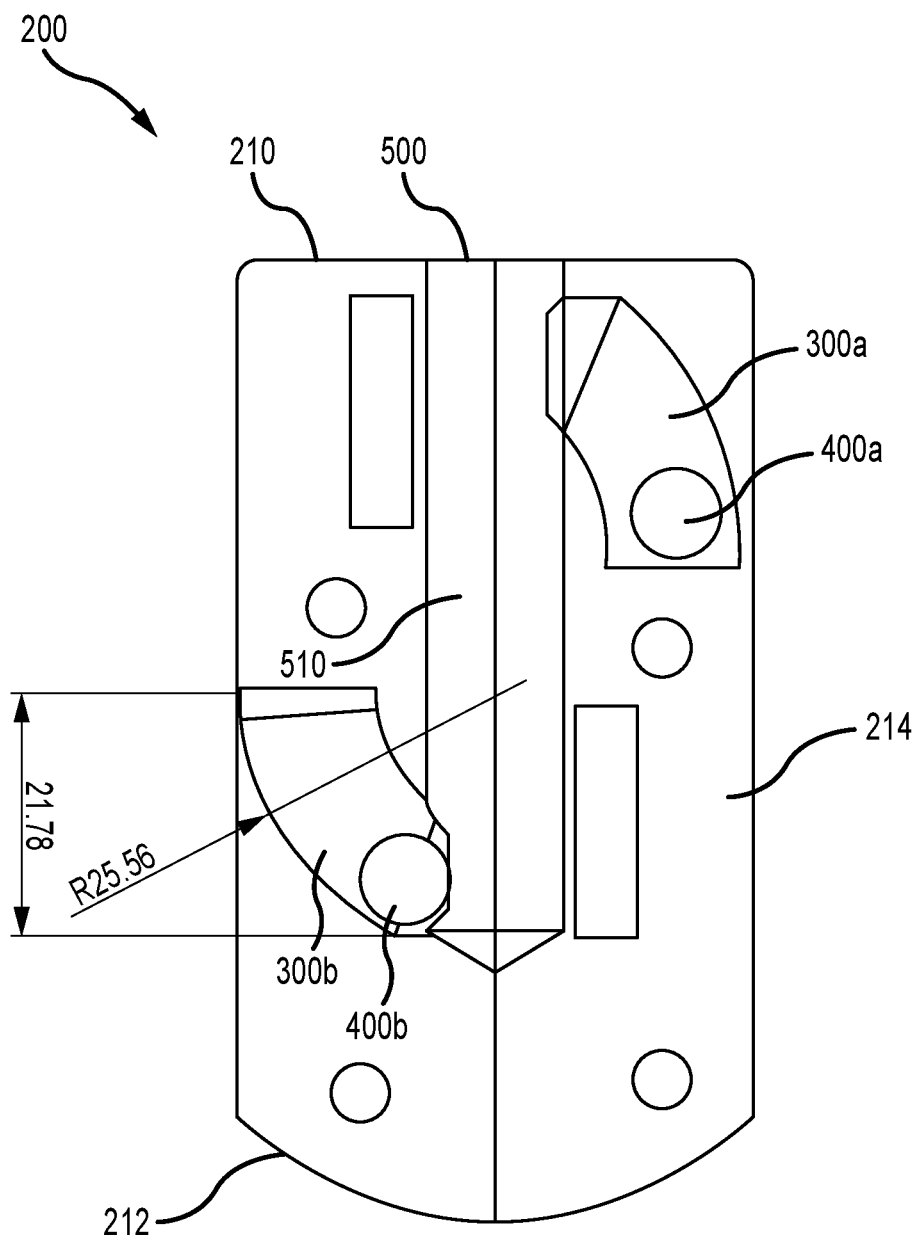
Figure 10:
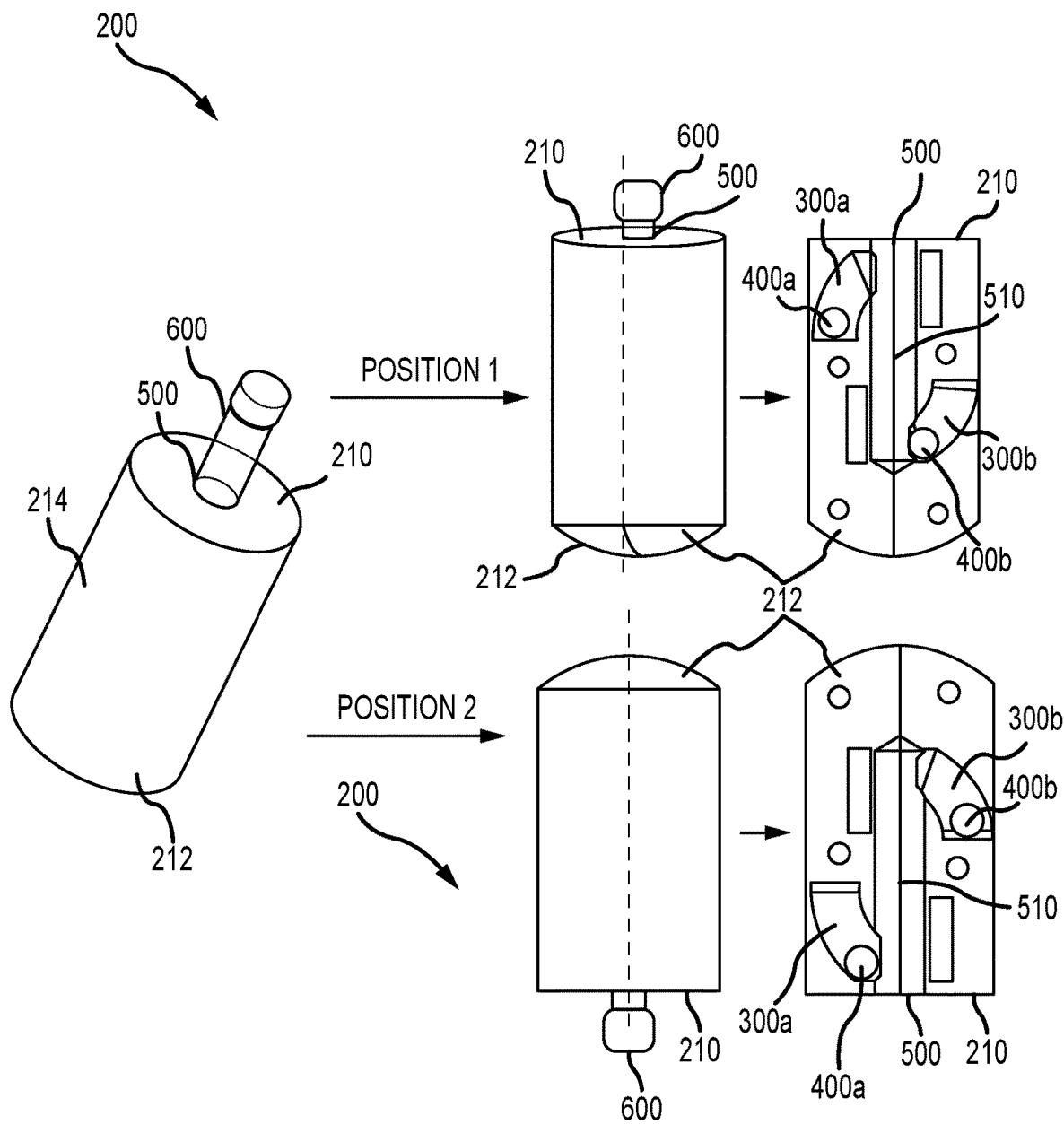
FIG. 10 is a schematic drawing illustrating one embodiment of how the sleeve device illustrated in FIGS. 9A-9B can be used for the magnetic separation of a biological entity from a fluid sample according to the present disclosure.

As used herein, the term "HERMES sleeve" is meant to broadly cover any magnetic separation chamber of the present disclosure that is in the form of a sleeve (see e.g., FIGS. 9A, 9B, and 10). Therefore, as used in this context, the term "HERMES" is not meant to limit the HERMES sleeve to the use of magnetic separation of "erythrocytes" from the fluid samples, but is meant to cover the use of the sleeve in the magnetic separation of any target biological entity from any type of fluid sample.

In one aspect, the present disclosure is directed to a device for use in magnetic separation of a target biological entity from a fluid sample. This device includes: (a) a magnetic separation chamber configured to receive a fluid sample for magnetic separation, wherein said magnetic separation chamber comprises at least two magnets mounted on the surface or in the wall of the magnetic separation chamber; and (b) a force provider configured to move the magnetic separation chamber in a side-to-side motion to mix and/or magnetize the fluid sample. In one embodiment, the magnetic separation chamber is in a form of a sleeve and comprises a substantially central channel for loading a vessel containing the fluid sample therein.

In one embodiment, the force provider is an actuator or a movable hand.

In one embodiment, the force provider is an actuator and the two magnets are mounted on opposing sidewalls a sufficient distance from one another so as to prevent interference between the magnetic field of each magnet, wherein the magnetic separation chamber is configured to receive and maintain the fluid sample at a position between the two magnets during operation of the device, and wherein the actuator is functionally coupled to the magnetic separation chamber, said actuator comprising a linear actuator configured to move the magnetic separation chamber laterally in a side-to-side motion so as to keep the two magnets in line with the fluid sample during operation of the actuator.

In one embodiment, the at least two magnets are fixed or movable along the wall of the magnetic separation chamber.

In one embodiment, the magnetic separation chamber further comprises at least two channels along the sidewall of the chamber to allow the at least two magnets movable in order to mix and magnetize the sample.

In one embodiment, the at least two channels are linear channels, curved channels, symmetric channels, cylindrical shaped, or tube shaped.

In one embodiment, the force provider is a manual force provider or an automatic force provider.

In one embodiment, the fluid sample further comprises at least an aggregation agent configured to group together an aggregate of a plurality of the target biological entities.

In one embodiment, the device further comprises a collection component for collecting a supernatant produced after capture and separation of the target biological entity from the fluid sample, and wherein the collection component is cap comprising capillary tube.

In one embodiment, the magnetic separation chamber comprising a durable plastic material or any other non-magnetic material.

In one embodiment, the at least two magnets are ball magnets.

In one embodiment, the ball magnets are 3/16 inch ball magnets (KJ Magnetics).

In one embodiment, the magnetic separation chamber is in a form of a sleeve and comprises a substantially central channel for loading a vessel containing the fluid sample therein.

In one embodiment, the substantially central channel has a circumference suitable for a standard blood collection tube.

In one embodiment, the substantially central channel has a circumference of approximately 10 mm and a depth of approximately 70-75 mm.

In one embodiment, the sleeve is configured to contain a vessel comprising a 3 mL tube.

In one embodiment, the vessel can contain a volume of fluid sample selected from the group consisting of up to 200 uL, up to 500 uL, up to 1 mL, up to 1.5 mL, up to 2.0 mL, up to 2.5 mL, up to 3.0 mL, and up to 5 mL.

In one embodiment, the vessels can contain a volume of fluid sample of 200 uL or greater.

In one embodiment, the sleeve is made with 3D printed plastic.

In one embodiment, the sleeve is made with injection molding techniques.

In one embodiment, the sleeve comprises dimensions approximating those of a 10 mL blood tube, said dimensions comprising approximately 16 mm in circumference and 100 mm in length for the depth of the substantially central channel, wherein total size of the sleeve can alternatively scale up or down according to these dimensions accordingly.

In one embodiment, the size of the sleeve can be scaled up at least by approximately 1.5 times.

In another aspect, the present disclosure is directed to a method for separating a target biological entity from a fluid sample. The method involves the steps of: (a) providing a device according to the present disclosure; (b) combining the fluid sample with a plurality of magnetic beads functionalized to bind to the target biological entity, wherein the combining is performed in a vessel comprising a tube or other suitable container for containing the fluid sample during operation of the device; (c) positioning the vessel containing the fluid sample and the functionalized magnetic beads between the two magnets of the magnetic separation chamber of the device; and (d) operating the device in a manner sufficient to capture the target biological entity on the functionalized magnetic beads, thereby yielding a supernatant free of or substantially free of said target biological entity.

In one embodiment this method further involves collecting the supernatant from the vessel.

In one embodiment this method further involves collecting and analyzing the supernatant and/or the captured target biological entity using one or more diagnostic tool or technique of interest.

In one embodiment, the method does not involve a centrifugation step to separate the target biological entity from the fluid sample.

In one embodiment, the magnetic beads are conjugated to an aggregation agent prior to the combining step, and wherein said aggregation agent is configured to group together an aggregate of a plurality of the target biological entities prior to the capture and separation of the target biological entity from the fluid sample.

In one embodiment, the aggregation agent is selected from the group consisting of an antibody, a protein, dextran, polyvinylpyrollidone, polyoxyethylene, fibrinogen, immunoglobulin IgM and IgG, calcium chloride, and combinations thereof.

In one embodiment, the target biological entity are red blood cells and the aggregation agent is an antibody that binds to red blood cells non-specifically, irrespective of blood type.

In one embodiment, the aggregation agent is an antibody that binds to a surface marker of red blood cells.

In one embodiment, the surface marker of the red blood cell is selected from the group consisting of CD235a and TER119.

In one embodiment, the plurality of magnetic beads and the aggregation agent are contained in a vessel comprising a tube or other suitable container for containing the fluid sample during operation of the device.

In one embodiment, the plurality of magnetic beads and the aggregation agent are provided together in a storage buffer.

In one embodiment, the plurality of magnetic beads are conjugated to the aggregation agent prior to adding the fluid sample.

In one embodiment, the plurality of magnetic beads and the aggregation agent are dried directly in a collection container prior to adding the fluid sample.

In one embodiment, the collection container is a vessel comprising a tube or other suitable container for containing the fluid sample during operation of the device.

In one embodiment, the target biological entity is selected from the group consisting of white blood cells, contaminants, waste products, and excess reagents contained in the fluid sample.

In one embodiment, this method further involves a collection component for collecting a supernatant produced after capture and separation of the target biological entity from the fluid sample.

In one embodiment, the collection component is a capillary tube configured to passively uptake the supernatant.

In one embodiment, the fluid sample is a blood sample, the target biological entity comprises red blood cells, and the supernatant comprises plasma.

Turning to FIGS. 9A-9B and 10, there is illustrated device 200 in the form of a sleeve for use in magnetic separation of a biological entity from a fluid sample according to the present disclosure. FIG. 9A illustrates an external view of sleeve device 200. FIG. 9B illustrates an internal cross-sectional view of sleeve device 200. As shown, sleeve device 200 includes magnetic separation chamber 214 having top portion 210 and bottom portion 212. As shown, bottom portion 212 can be curved, but need not be. Top portion 210 includes opening 500 of substantially central channel 510. Substantially central channel 510 is where vessel 600 (containing the fluid sample) is housed during operation of sleeve device 200. As shown in FIG. 9B, sleeve device 200 includes substantially central channel 510 and two side channels (300a, 300b) that each contain magnets (400a, 400b).

FIGS. 9A and 9B and position 1 of FIG. 10 show sleeve device 200 oriented in an upright position, where top portion 210 is facing up and bottom portion 212 is facing down. As shown in FIG. 10, in this upright position (position 1, FIG. 10), magnet 400a of side channel 300a is a farther distance away from substantially central channel 510 as compared to magnet 400b of side channel 300b. Further, in this orientation, the bulk of the fluid sample containing the target biological entity will collect in vessel 600 toward the bottom of vessel 600 (also the bottom of substantially central channel 510). As depicted in FIG. 10 (position 1), this also results in magnet 400b coming into contact to the right side of substantially central channel 510. Therefore, as shown in FIG. 10, during operation, when sleeve device 200 is moved to an upside down position (position 2), where top portion 210 is facing down and bottom portion 212 is facing up, vessel 600 will be inverted with the bulk of the fluid sample being at the top of vessel 600. Also in this upside down position (position 2, FIG. 10), magnet 400a contained in side channel 300a will be a closer distance to the substantially central channel 510 compared to magnet 400b of side channel 300b. As depicted in FIG. 10 (position 2), this also results in magnet 400a of side channel 300a coming into contact to the left side of substantially central channel 510. Continuous inversions of sleeve device 200 from the upright position to the upside down position results in lateral mixing of the contents of the fluid sample due to the side-to-side magnetic field changes, as well as gravitational mixing of the fluid in a longitudinal manner within vessel 600.

In certain embodiments, the HERMES sleeve offers portable separation capabilities for blood for sample volumes of up to 1.5 mL, without limitation. The HERMES sleeve capitalizes on the innovation of the original portable benchtop HERMES device and system as described herein. The sleeve mimics the lateral mixing of the benchtop HERMES device while taking advantage of bulk-scale mixing that is generally created by end-over-end mixing. In certain embodiments, this sleeve may be more appropriate for use in the field and other translational settings.

In certain embodiments, the benefit of this sleeve is at least two-fold: (a) the sleeve is resource independent and fully self-sufficient; and (b) the sleeve is compatible with macroscale volumes (up to 1.5 mL).

In certain examples, the HERMES sleeve has been tested with 7 human samples. All human samples were tested with 1.5 mL of blood. The experiments were sufficient to attain an average purity of 99.9% with a yield of 67%. In one example, the sleeve was designed much like a commercially available tube holder. In this example, the sleeve was cylindrical in shape and includes a hole in the center to mount a standard blood collection tube. Inside the sleeve, there were 2 chambers that each housed a high strength spherical ball magnet (e.g. 3/16 inch ball magnet purchases from KJ Magnetics). As seen in FIG. 10, the configuration of the magnets with respect to the sample changes as the tube is inverted.

During operation of certain examples of the HERMES sleeve, once the sample is collected in the tube it can be placed in the HERMES sleeve for mixing. Mixing is facilitated by inversion. As shown FIG. 10, in position 1, the beads are magnetized on the left-hand side of the tube, while in position 2 (inverted), the beads are magnetized on the right-hand side. This setup mimics the lateral mixing that was created by the original benchtop HERMES device and combines it with inertial mixing that is enabled by gravity. One advantage of this embodiment is that this protocol was designed to require minimal training: standard protocol for plasma collection requires the inversion of the collection tube for 5-7 times to ensure that the anticoagulant is mixed evenly. The HERMES sleeve takes advantage of this requirement to perform the effective mixing of magnetic beads and aggregation agent.

EXAMPLES

The following examples are intended to illustrate particular embodiments of the present invention, but are by no means intended to limit the scope of the present invention.

Example 1

H.E.R.M.E.S: Rapid Blood-Plasma Separation at the Point-of-Need

Abstract

The global healthcare landscape is experiencing increasing demand for CLIA-waived testing facilities that offer diagnostic capabilities at lower costs and greater convenience than traditional laboratory testing. While several new diagnostic tools have emerged to fulfill testing requirements in these environments, centrifuges have been stymied from transitioning to the point-of-need as the US Food and Drug Administration (FDA) classifies them as mostly unsuitable for use in CLIA-waived environments. Limitations in sample processing capabilities adversely affects the ability for CLIA-waived testing environments to offer a broad testing portfolio and present-day diagnostics are bottlenecked by the requirement for centrifugation. Here we present the High Efficiency Rapid Magnetic Erythrocyte Separator (H.E.R.M.E.S), a rapid low-cost technology that can perform the separation of red blood cells from plasma at a fraction of the time and cost of that of a centrifuge. We demonstrate that H.E.R.M.E.S is able to obtain highly-pure plasma (greater than 99.9% purity) at less than 2 minutes per test. Further, we detail that it is an easy-to-use method capable of being incorporated with present-day diagnostic technologies and prove that it is superior to existing alternatives to centrifugation by validation with a ferritin lateral flow test. H.E.R.M.E.S is a suitable alternative for centrifugation in point-of-need settings and aims to facilitate the decentralization of commercial blood testing.

H.E.R.M.E.S Device Design Landscape:

H.E.R.M.E.S has been designed with a specific intention of being easy-to-use. The process involves three main phases: capture, separation and extraction. In order to obtain separated plasma, the user need only follow three steps (as outlined in FIG. 4A), i) collect the sample (typically with a finger-stick) and load the sample in a test tube precoated with functionalized magnetic beads, ii) place sample in H.E.R.M.E.S and wait for 2 minutes, iii) remove sample and extract plasma using a capillary tube. Once the sample has been extracted, the sample can be used for further analysis or stored for future use.

Figure 4B:
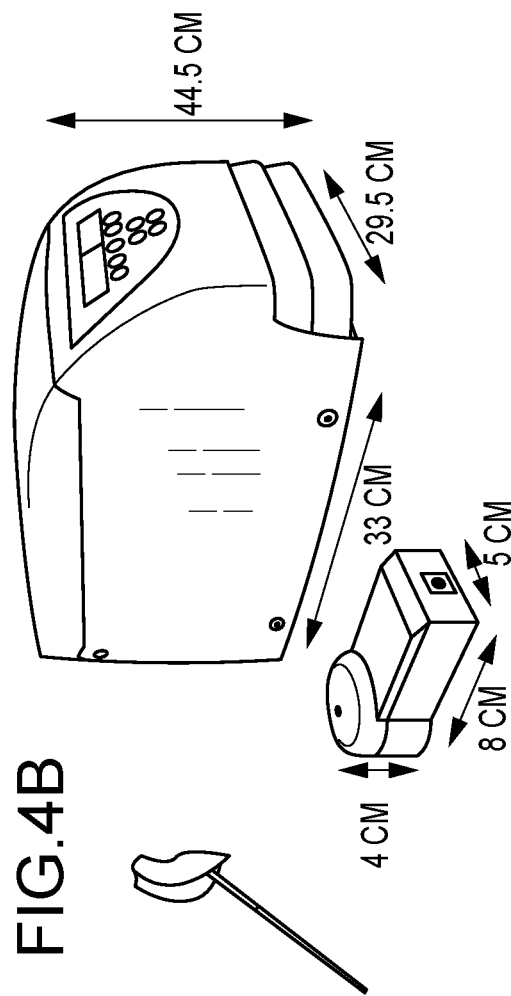
FIGS. 4A-4D are schematic drawings of embodiments of the device, system, and method of the present disclosure.
Figure 4D:
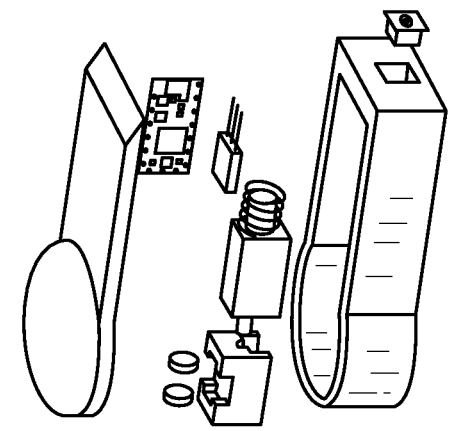
Figure 4A:
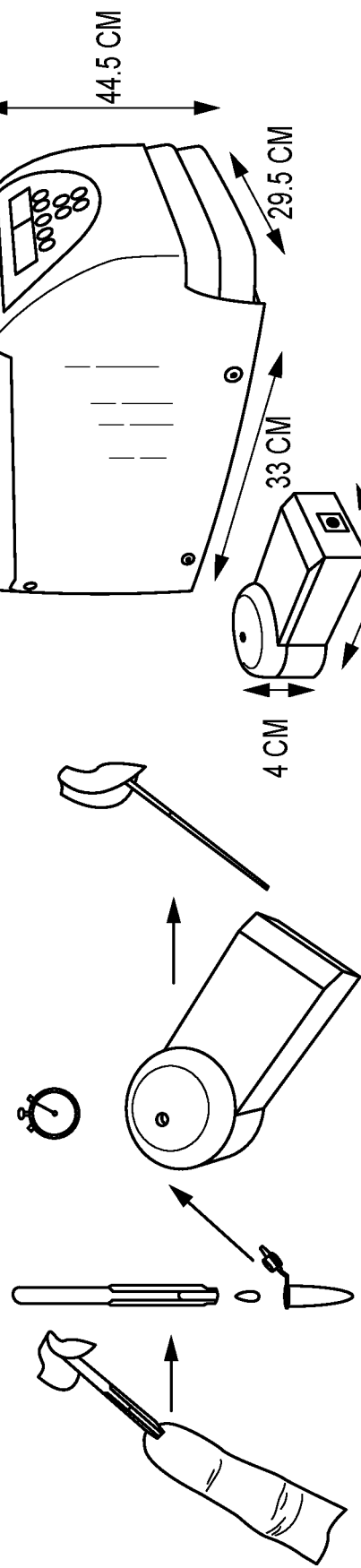
Figure 4C:
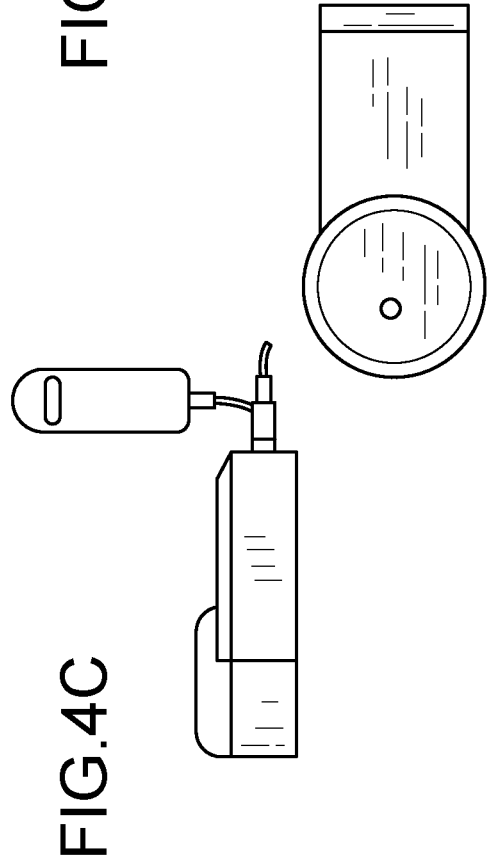
Figures 5A, 5B:
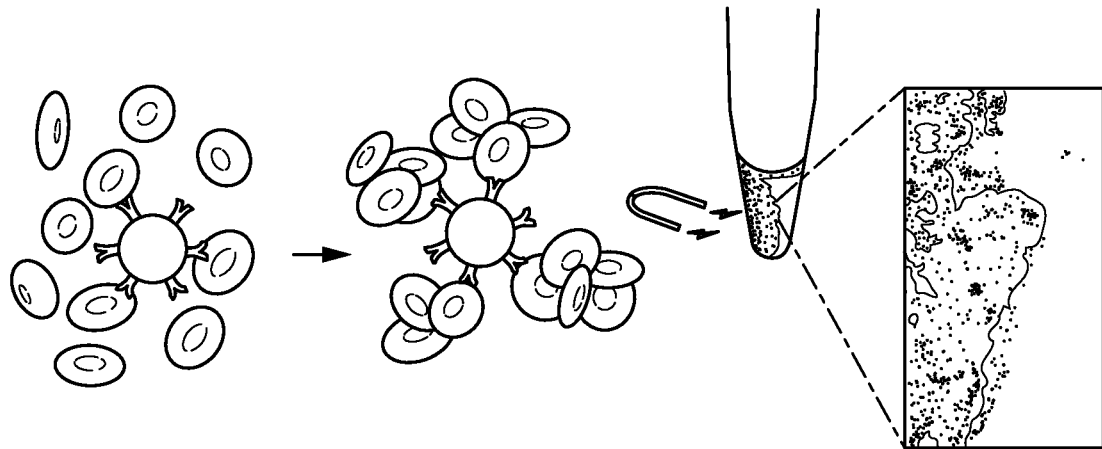
FIGS. 5A-5B illustrate how a target biological entity (red blood cells) are aggregated and captured using an aggregation agent and functionalized magnetic beads.

The portable benchtop device itself consists simple onboard electronics to enable automation (FIG. 4D). H.E.R.M.E.S employs a small linear solenoid that actuates a magnetic field in a specific direction with respect to the sample to create a mixing effect. This ensures that the beads are able to capture the erythrocytes in the sample. The device occupies a small footprint and can be powered by any standard electrical outlet. Once the device is plugged in, the actuation starts automatically and proceeds for 90 seconds. After 90 seconds, the solenoid turns off and the magnetic beads are concentrated by the magnet on one side of the sample holder. The user then employs a small capillary tube to uptake the separated plasma. While the current iteration requires the use of an outlet, it can be easily re-engineered to include a portable battery pack instead. H.E.R.M.E.S was specifically designed to enable sample processing in point-of-need settings and was designed for semi-autonomous operation to minimize the need for manual intervention by the user.

Magnetic Bead Capture of Erythrocytes:

Magnetic bead based capture has been adopted several biological applications such as DNA extraction, peptidome assessment and immunocapture (22-24). The technique is particularly useful for capturing a small amount of analyte as the beads can be concentrated to yield a higher limit of detection (25). H.E.R.M.E.S tackles the opposite problem: a single microliter of human blood can contain up to 6 million blood cells. This resulted in a significant challenge as it was necessary to capture all the erythrocytes in the sample without the need for dilution.

At first glance, it would appear a simple assessment of the binding capacity of the magnetic beads would be sufficient in order determine the minimum number of beads required to capture all the blood cells in the sample. A "brute force" approach as such would be appropriate for separation but would suffer from a lack of scalability. Further, this approach would have a fragile dependence on the sample size with a cost-scaling directly proportional to the number of cells that would need to be captured. In order to maintain a cost-effective scaling principle, H.E.R.M.E.S uses an aggregation agent that groups red blood cells together during the capture phase, thereby reducing the effective number of cells that need to be captured (See FIG. 2). By aggregating the cells prior to the capture, we are able to demonstrate an approximate 2000-fold increase in binding capacity of the beads using this aggregation agent. H.E.R.M.E.S is unique in comparison to previous works in literature that employ aggregation enhanced capture as it is performed in an easily accessible format that does not require specialized filtration paper or microfluidic setup (26,27). Our estimations reveal that on average, one bead is able to capture up to 100 cells due to the aggregation effect. Approximately 5.4 mg of blood cells are captured with close to a tenth of the amount of beads.

Evaluation of H.E.R.M.E.S Using Human Samples

Figure 6:
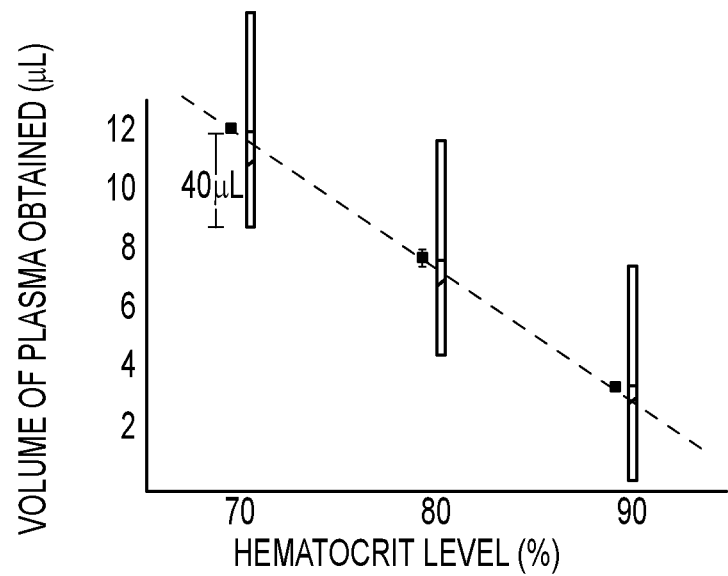
FIG. 6 is a graph illustrating separation of plasma from human samples with artificially high hematocrit values. Each sample was tested in duplicate and the standard deviation for each sample set is indicated with error bars (n=2). An average purity of 99.9% was obtained in these samples.

We used H.E.R.M.E.S to process blood samples from 15 individuals and analyzed the plasma obtained after extraction (Table 1). We demonstrate an average purity greater than 99.9% (less than 20 cells/µL counted) and an average extraction time of 108 seconds to obtain 90% of the available plasma. H.E.R.M.E.S demonstrates a high efficiency to capture and separate red blood cells irrespective of blood type and hematocrit levels. To further demonstrate the ability of aggregation to enhance the capture rate, we used H.E.R.M.E.S to separate erythrocytes in artificially spiked blood samples that have abnormally high hematocrit (FIG. 6). We hypothesize that the aggregation effect scales non-linearly with an increase in the number of red blood cells. The high concentration of blood cells decreases the interaction space leading to effective binding in these samples. H.E.R.M.E.S can perform reliably with an increase in red blood cells and is able to obtain highly pure plasma regardless of the number of blood cells. Factoring in the cost of the aggregation agent and the beads, we expect H.E.R.M.E.S to cost less than $2 per separation test.

TABLE 1

| | |
|---|---|
| Average Purity of Obtained Plasma | 99.95 ± 0.05% |
| Average Time for Extraction | 108 ± 21 seconds |
| Average Volume Obtained | 17.2 ± 1.96 µL |

As shown in Table 1, data collected from testing 15 human blood samples with varying ages, hematocrits and blood types. A starting volume of 40 µL was used for each test. Samples were run in duplicate and the standard deviation is reported. Average volume of uncontaminated plasma obtained from centrifugation was 18.2 µL. All samples were purified using 0.625 mg of magnetic beads and 200 µg of aggregation agent.

Quantifying the Effect of Aggregation on Performance

Figure 7A:
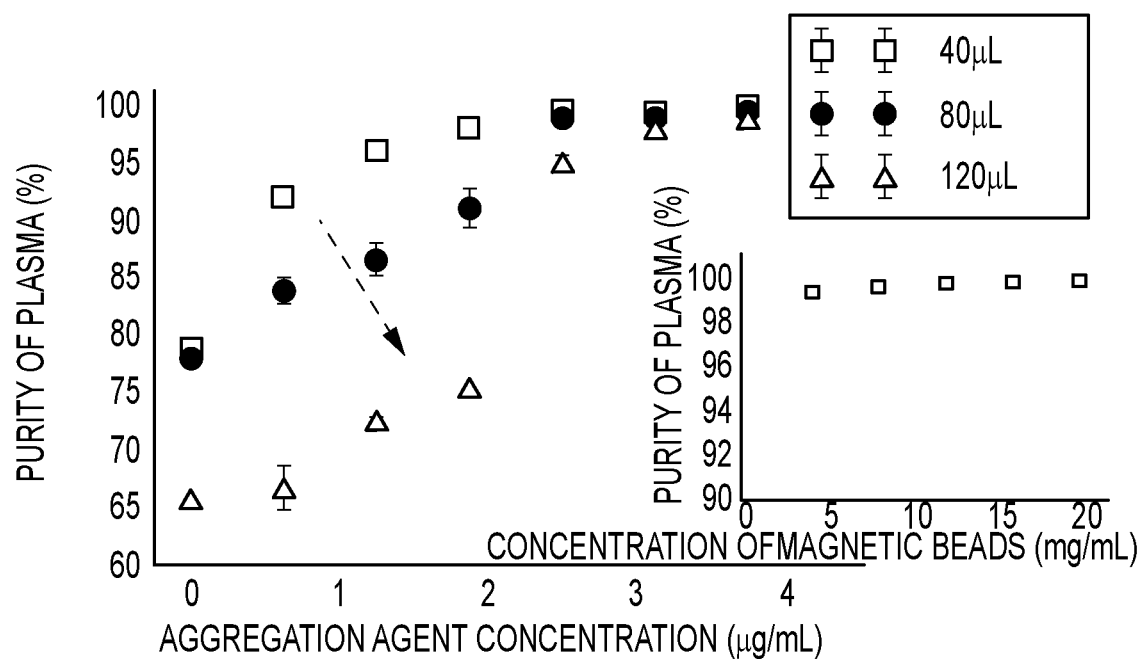
FIGS. 7A-7B illustrate the effect of the aggregation agent on performance of the H.E.R.M.E.S. methodology.
Figure 7B:
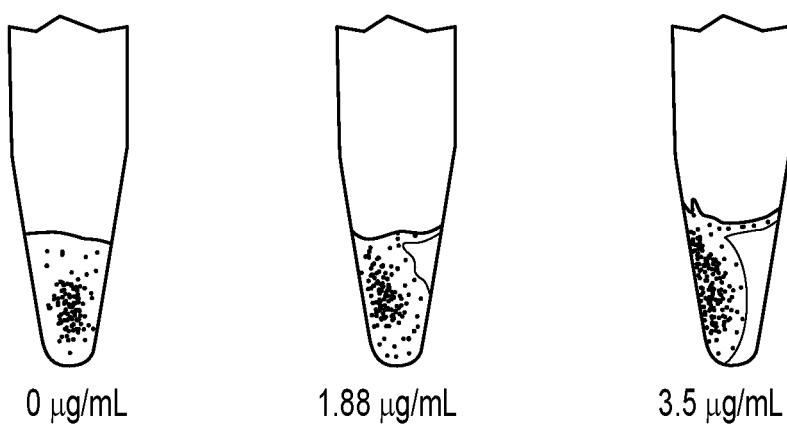

Aggregation reduces the number of effective targets that need to be captured to obtain highly pure plasma. To understand the dependence of the aggregation capabilities on separation performance, we tested the cell capture rate with varying levels of aggregation agent. The cell capture rate was indirectly inferred by calculating the purity of the plasma obtained after separation. We then compared the purity of plasma obtained using different sample volumes to assess the scalability of the technique. As seen in FIG. 7, it can be noted that a concentration of about 3.5 ug/mL of aggregation agent is sufficient to obtain plasma of high purity (greater than 99%). We also observe a non-linear relationship wherein the binding capacity is amplified several-fold as the amount of agent is increased. We expect the curve to be pushed further out in the regime where the concentration of the aggregation agent is low. However, there exists a critical concentration that creates the level of aggregation necessary to obtain highly pure plasma (greater than 99%). In contrast, we also studied the effect of increasing the number of magnetic beads on performance and noted that the amount of beads does not significantly affect the separation of performance.

Integration with Existing Diagnostic Testing Platforms

Figure 8A:
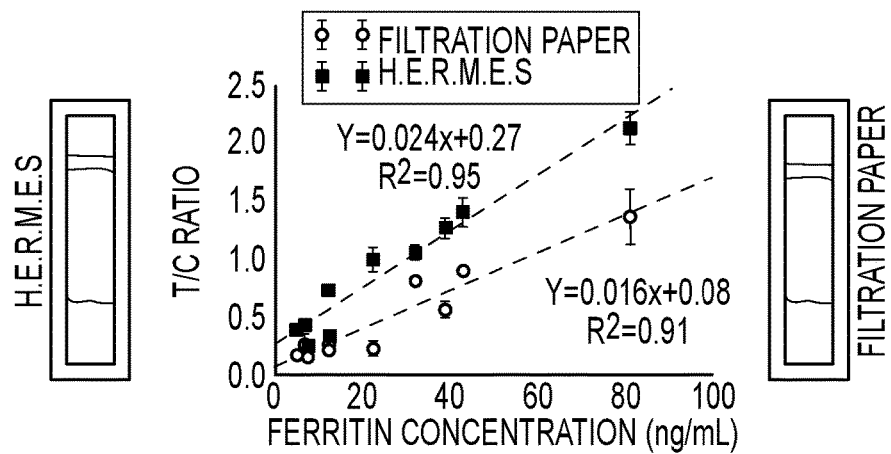
FIGS. 8A-8C illustrate the performance of various aspects of the H.E.R.M.E.S methodology.
Figure 8B:
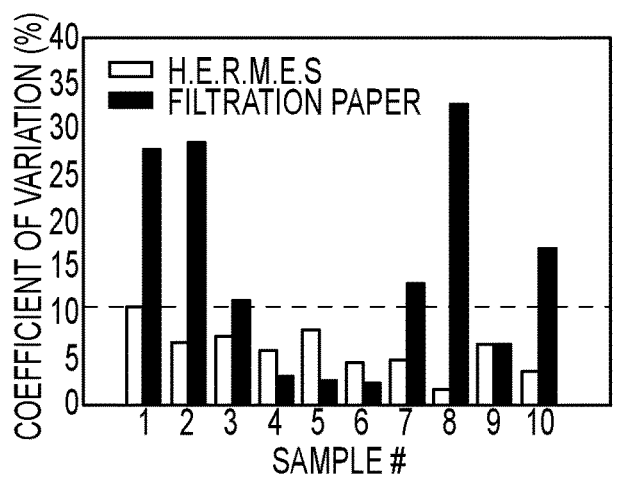
Figure 8C:
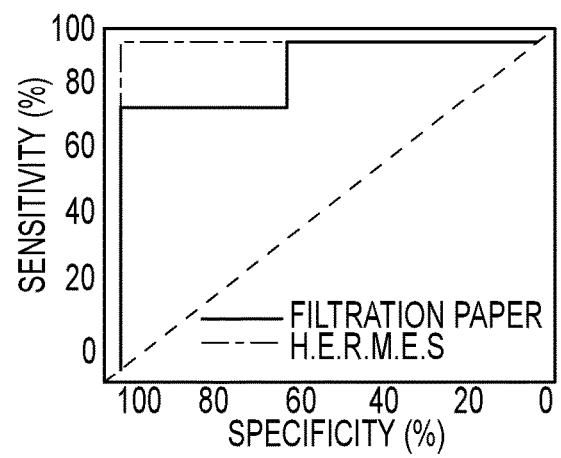

We demonstrate the ability of H.E.R.M.E.S to augment the performance of present day diagnostics by incorporating the technology with lateral flow test strips—a common diagnostic platform often implemented for use at the point-of-need. Ferritin lateral flow strips previously described by Srinivasan et al. (28) were tested using 10 human blood samples. We compared the performance of H.E.R.M.E.S against commercially available filtration paper (MDI). A calibration curve was built with a linear trendline fit to compare the performance of the two test cases (FIG. 8). In general, we observed that H.E.R.M.E.S leveraged higher quantitative power from the regression model used in each of these cases. ROC curves were plotted using the Delong method (29) and a difference in performance was established. Further, as seen in FIG. 8 a higher slope (46%) was noted for test strips that incorporated plasma obtained from H.E.R.M.E.S indicating greater quantitative ability across the concentration range of interest. More importantly, H.E.R.M.E.S was able to demonstrate a significantly reduced average coefficient of variation (6% vs 21%) further proving that it is capable of advancing the performance of point-of-need testing platforms.

Discussion and Conclusion

H.E.R.M.E.S leverages the elementary concept of magnetic separation to carry out a challenging process of separating unwanted cellular material from a sample. The method was specifically designed to be low-cost, rapid and minimally complex. The system was designed to allow for maximal automation and minimal intervention from the user while maintaining a low-cost. These characteristics make H.E.R.M.E.S a promising alternative to the traditional lab centrifuge in settings where a centrifuge cannot operate, whether due to regulatory constraints or resource limitations. Further, while we validated H.E.R.M.E.S with a commonly available point-of-need testing platform (lateral flow tests), it is universal and can be used to simplify purification for virtually any diagnostic test that requires plasma or serum as an input. While there are a handful of sophisticated commercial platforms that are capable of performing immunoassay chemistry without the need for separating red blood cells, H.E.R.M.E.S will enable the use of standard diagnostic techniques in low-resource settings where other alternatives are not feasible. Further, the high recovery rate (>90% of available serum), the low time for recovery, the low cost and ease of use of the system make it superior to solutions that have been demonstrated in literature (5, 8, 30).

H.E.R.M.E.S has the potential to impact the blood testing industry due to its ability to offer the separation efficiency of a centrifuge at a fraction of the time and cost. H.E.R.M.E.S seeks to facilitate the implementation of present-day diagnostic tools at the point-of-need by integrating into CLIA-waived testing environments where centrifuges are currently unable to operate. H.E.R.M.E.S can enable rapid front-end sample processing to help prevent loss of sample quality in these environments by ensuring that all red blood cells are removed prior to clinical chemistry testing. We envision H.E.R.M.E.S having immediate applicability in advancing molecular diagnostics such as PCR to the point-of-need as it can integrate easily in to existing methods for translational PCR. Particularly, the isolation of white blood cells makes an interesting use case for infectious disease detection (31, 32) and genetic sequencing (33). In addition to being highly scalable due to the low cost of raw materials that are involved in fabrication, H.E.R.M.E.S is able to perform highly efficient blood plasma separation within 2 minutes at less than $2 per test and is suitable for use in resource-limited settings. While the current iteration of H.E.R.M.E.S is only capable of accommodating one sample, we envision that a future prototype will possess parallel sample processing capabilities as the underlying technique is highly scalable. Further, the stand-alone system is easy to use and can be adopted by users irrespective of their prior medical training making the H.E.R.M.E.S a unique method to perform blood-plasma separation at the point-of-need.

Materials and Methods

Preparing Magnetic beads: Magnetic beads (ProMag HP, Bangs Labs) suspended in a 50 mM IVIES Buffer were conjugated to a Anti Red Blood Cell antibody (Rockland Antibodies) by incubating the sample in an end-over-end mixer for 12-15 hours. After conjugation, the supernatant was removed and replaced with a storage buffer (10 mM Tris Buffer, pH 8, 0.05% Bovine Serum Albumin, 0.05% Proclin 300). The beads were stored at 4-8° C. in liquid form and are stable up to several months. Prior to testing, 325 µg of beads and 200 µg of antibody were loaded in a single PCR tube (Eppendorf) and dried in a vacuum centrifuge (Eppendorf Vacufuge 5301) for 30 minutes. The antibody is added separately to induce clumping of the red blood cells to reduce the number of effective targets during the capture process. Dried beads were then used for tests or stored at 4-8° C. The dried beads demonstrated a shelf life of up to three months when sealed in a dark container.

H.E.R.M.E.S benchtop unit: A small portable benchtop unit was designed in Sledworks and printed using a Objet 3D printer. The device itself consists of a microcontroller (Teensy 3.2, Sparkfun), a few transistors and a 12V actuating solenoid (Adafruit Industries). Two circular neodymium magnets (K&J Magnetics) were mounted on a 3D printed holder and attached to the solenoid. The device also has a power input jack that can be connected to standard 12V, 0.5 A wall power supply.

Analysis of Plasma: Upon separation of plasma from the red blood cells using H.E.R.M.E.S, a capillary tube (Microcaps, Drummond Scientific) was used to extract the serum from the sample and transferred into another test tube. Once transferred, the serum was diluted 5 times and mixed in a 1:1 ratio with trypan blue stain. Once stained, the serum was loaded into a disposable hemocytometer (C-Chip, Cyto Diagnostics) and cell counting was performed under a bright field microscope. The number of cells counted were then used to estimate the purity of the plasma obtained.

High Hematocrit Samples: Blood samples with abnormal hematocrits were prepared with type 0 human red blood cells suspended in alsever's solution (Innovative Research). The blood cells were spun down and concentrated in a centrifuge and resuspended to abnormally high hematocrit values (70, 80 and 90%)

Lateral Flow Test: Ferritin strips were manufactured similar to work mentioned in Srinivasan et al. We prepared two batches of test strips with blood filtration membranes (Type FR-1 (0.35) MDI membrane technologies) used as a sample pad. The FR-1 is a passive forward flowing filtration membrane that has a thickness of 0.35 mm and capacity of 30 µL/cm$^2$. 10 human blood samples (Innovative Research) were then used for testing. For the strips that used the filtration membranes, a 3-minute incubation period was added at the beginning of the test to allow the plasma to filter through the membrane. This was followed by the application of 40 uL of running buffer to start the test. For the test cases that used plasma from H.E.R.M.E.S, the test was immediately started by using a 15 µL the capillary tube to apply the plasma onto the sample pad followed by application of 40 µL of running buffer. We note that these test strips could also have been used as a dipstick format, wherein the sample pad is dipped in the sample holder to start the test. After 30 minutes, the test strips were imaged using the TIDBIT (previously mentioned by Lu et al. (34)) and a calibration curve was built using custom python code. Actual ferritin values were obtained using a SIEMENS Immulite1000 immunoassay analyzer.

REFERENCES

Citation of a reference herein shall not be construed as an admission that such reference is prior art to the present invention. All references cited herein are hereby incorporated by reference in their entirety. Below is a listing of various references relating to the present disclosure:
1. Global Blood Testing Market Size & Share|Industry Report, 2018-2024 [Internet]. [cited 2018 Jun. 14]. Available from: https://www.grandviewresearch.com/industry-analysis/blood-testing-market
2. Al-Soud W A, Radstrom P. Purification and Characterization of PCR-Inhibitory Components in Blood Cells. J Clin Microbiol. 2001 Feb. 1; 39(2):485-93.
3. Mabey D, Peeling R W, Ustianowski A, Perkins M D. Diagnostics for the developing world: Tropical infectious diseases. Nat Rev Microbiol. 2004 March; 2(3):231-40.
4. Recommendations for Clinical Laboratory Improvement Amendments of 1988 (CLIA) WaiverApplications for Manufacturers of In Vitro Diagnostic Device—Guidance for Industry and Food and Drug Adminstration Staff [Internet]. United States Food and Drug Adminstration (FDA); 2008. Available from: https://www.fda.gov/downloads/MedicalDevices/DeviceRegulationandGuidance/GuidanceDocuments/ucm070890.pdf
5. Liu C, Mauk M, Gross R, Bushman F D, Edelstein P H, Collman R G, et al. Membrane-Based, Sedimentation-Assisted Plasma Separator for Point-of-Care Applications. Anal Chem. 2013 Nov. 5; 85(21):10463-70.
6. Posthuma-Trumpie G A, Korf J, van Amerongen A. Lateral flow (immuno)assay: its strengths, weaknesses, opportunities and threats. A literature survey. Anal Bioanal Chem. 2009 January; 393(2):569-82.
7. Xu Q, Xu H, Gu H, Li J, Wang Y, Wei M. Development of lateral flow immunoassay system based on superparamagnetic nanobeads as labels for rapid quantitative detection of cardiac troponin I. Mater Sci Eng C. 2009 April; 29(3):702-7.
8. Son J H, Lee S H, Hong S, Park S, Lee J, Dickey A M, et al. Hemolysis-free blood plasma separation. Lab Chip. 2014; 14(13):2287-92.
9. Mielczarek W S, Obaje E A, Bachmann T T, Kersaudy-Kerhoas M. Microfluidic blood plasma separation for medical diagnostics: is it worth it? Lab Chip. 2016; 16(18):3441-8.
10. Kersaudy-Kerhoas M, Sollier E. Micro-scale blood plasma separation: from acoustophoresis to egg-beaters. Lab Chip. 2013; 13(17):3323.
11. Gossett D R, Weaver W M, Mach A J, Hur S C, Tse H T K, Lee W, et al. Label-free cell separation and sorting in microfluidic systems. Anal Bioanal Chem. 2010 August; 397(8):3249-67.
12. Bhagat A A S, Bow H, Hou H W, Tan S J, Han J, Lim C T. Microfluidics for cell separation. Med Biol Eng Comput. 2010 October; 48(10):999-1014.
13. Chen X, Cui D, Liu C, Li H. Microfluidic chip for blood cell separation and collection based on crossflow filtration. Sens Actuators B Chem. 2008 Mar. 14; 130(1):216-21.
14. Chin C D, Linder V, Sia S K. Commercialization of microfluidic point-of-care diagnostic devices. Lab Chip. 2012; 12(12):2118.
15. Brown J, Theis L, O'Connor K, Kerr L, Uthman M, Oden Z M, et al. A Hand-Powered, Portable, Low-Cost Centrifuge for Diagnosing Anemia in Low-Resource Settings. Am J Trop Med Hyg. 2011 Aug. 1; 85(2):327-32.
16. Wong A P, Gupta M, Shevkoplyas S S, Whitesides G M. Egg beater as centrifuge: isolating human blood plasma from whole blood in resource-poor settings. Lab Chip. 2008; 8(12):2032.
17. Bhamla M S, Benson B, Chai C, Katsikis G, Johri A, Prakash M. Hand-powered ultralow-cost paper centrifuge. Nat Biomed Eng. 2017 Jan. 10; 1(1):0009.
18. Mariella R. Sample preparation: the weak link in microfluidics-based biodetection. Biomed Microdevices. 2008 December; 10(6):777-84.
19. Street P. Requirements for high impact diagnostics in the developing world.:8.
20. Dineva M A, Mahilum-Tapay L, Lee H. Sample preparation: a challenge in the development of point-of-care nucleic acid-based assays for resource-limited settings. The Analyst. 2007; 132(12):1193.
21. Plebani M. Does POCT reduce the risk of error in laboratory testing? Clin Chim Acta. 2009 June; 404(1):59-64.
22. Caldarelli-Stefano R, Vago L, Bonetto S, Nebuloni M, Costanzi G. Use of magnetic beads for tissue DNA extraction and IS6110 Mycobacterium tuberculosis PCR. Mol Pathol. 1999 Jun. 1; 52(3):158-60.

23. Fiedler G M, Baumann S, Leichtle A, Oltmann A, Kase J, Thiery J, et al. Standardized Peptidome Profiling of Human Urine by Magnetic Bead Separation and Matrix-Assisted Laser Desorption/Ionization Time-of-Flight Mass Spectrometry. Clin Chem. 2007 Mar. 1; 53(3):421-8.
24. Sista R S, Eckhardt A E, Srinivasan V, Pollack M G, Palanki S, Pamula V K. Heterogeneous immunoassays using magnetic beads on a digital microfluidic platform. Lab Chip. 2008; 8(12):2188.
25. Tang D, Zhong Z, Niessner R, Knopp D. Multifunctional magnetic bead-based electrochemical immunoassay for the detection of aflatoxin B1 in food. The Analyst. 2009; 134(8):1554.
26. Tripathi S, Prabhakar A, Kumar N, Singh S G, Agrawal A. Blood plasma separation in elevated dimension T-shaped microchannel. Biomed Microdevices. 2013 June; 15(3):415-25.
27. Yang X, Forouzan O, Brown T P, Shevkoplyas S S. Integrated separation of blood plasma from whole blood for microfluidic paper-based analytical devices. Lab Chip. 2012; 12(2):274-80.
28. Srinivasan B, O'Dell D, Finkelstein J L, Lee S, Erickson D, Mehta S. iron Phone: Mobile device-coupled point-of-care diagnostics for assessment of iron status by quantification of serum ferritin. Biosens Bioelectron. 2018 January; 99:115-21.
29. DeLong E R, DeLong D M, Clarke-Pearson D L. Comparing the areas under two or more correlated receiver operating characteristic curves: a nonparametric approach. Biometrics. 1988 September; 44(3):837-45.
30. Yeh E-C, Fu C-C, Hu L, Thakur R, Feng J, Lee L P. Self-powered integrated microfluidic point-of-care low-cost enabling (SIMPLE) chip. Sci Adv. 2017 March; 3(3):e1501645.
31. Whitby D, Boshoff C, Hatzioannou T, Weiss R., Schulz T., Howard M., et al. Detection of Kaposi sarcoma associated herpesvirus in peripheral blood of HIV-infected individuals and progression to Kaposi's sarcoma. The Lancet. 1995 September; 346(8978):799-802.
32. Wang W-K, Sung T-L, Tsai Y-C, Kao C-L, Chang S-M, King C-C. Detection of Dengue Virus Replication in Peripheral Blood Mononuclear Cells from Dengue Virus Type 2-Infected Patients by a Reverse Transcription-Real-Time PCR Assay. J Clin Microbiol. 2002 Dec. 1; 40(12): 4472-8.
33. Sigurdson A J, Hauptmann M, Chatterjee N, Alexander B H, Doody M M, Rutter J L, et al. Kin-cohort estimates for familial breast cancer risk in relation to variants in DNA base excision repair, BRCA1 interacting and growth factor genes. BMC Cancer [Internet]. 2004 December [cited 2018 Sep. 5]; 4(1). Available from: http://bmccancer.biomedcentral.com/articles/10.1186/1471-2407-4-9
34. Lu Z, O'Dell D, Srinivasan B, Rey E, Wang R, Vemulapati S, et al. Rapid diagnostic testing platform for iron and vitamin A deficiency. Proc Natl Acad Sci. 2017 Dec. 19; 114(51):13513-8.

First Set of Examples of Embodiments of the Present Disclosure

A1. A device for use in magnetic separation of a target biological entity from a fluid sample, said device comprising:
a magnetic separation chamber configured to receive a fluid sample for magnetic separation, wherein said magnetic separation chamber comprises two magnets mounted on opposing sidewalls a sufficient distance from one another so as to prevent interference between the magnetic field of each magnet, and wherein the magnetic separation chamber is configured to receive and maintain the fluid sample at a position between the two magnets during operation of the device; and an actuator functionally coupled to the magnetic separation chamber, wherein said actuator comprises a linear actuator configured to move the magnetic separation chamber laterally in a side-to-side motion so as to keep the two magnets in line with the fluid sample during operation of the actuator.

A2. The device according to A1, wherein the magnetic separation chamber is configured to receive a fluid sample having a volume of up to 200 microliters.

A3. The device according to A1, wherein the magnetic separation chamber is configured to receive a vessel comprising a tube or other suitable container containing the fluid sample.

A4. The device according to A1, wherein the magnets are circular magnets.

A5. The device according to A1, wherein the magnets are neodymium magnets.

A6. The device according to A1, wherein the actuator is an actuating solenoid [linear actuator solenoid].

A7. The device according to A6, wherein the actuating solenoid is a 12 volt actuating solenoid.

A8. The device according to A1 further comprising a housing unit configured to house the magnetic separation chamber and the actuator.

A9. The device according to A8, wherein the housing unit comprises a base portion and a top cover portion, wherein the base portion is configured to hold the magnetic separation chamber and the actuator, and wherein the top cover portion is configured to fit over and cover the base portion and its contents.

A10. The device according to A9, wherein the top cover portion further comprises an opening for inserting the fluid sample into a position between the two magnets of the magnetic separation chamber.

A11. The device according to A8, wherein the housing unit is configured to further house onboard electronics components effective to operate the actuator and to enable automation of the device.

A12. The device according to A11, wherein the onboard electronics components comprise at least one component selected from the group consisting of a microcontroller, a transistor, and a power input jack.

A13. The device according to A12, wherein the power input jack is suitable for use with a standard 12 volt, 0.5 ampere wall power supply.

A14. The device according to A1, wherein the device is in a form of a portable benchtop device.

A15. The device according to A14, wherein the portable benchtop device has dimensions not greater than 4 centimeters in height, 5 centimeters in width, and 8 centimeters in length.

A16. The device according to A1, wherein the device is in a form suitable for use for point-of-need diagnostics of the fluid sample.

B1. A system for use in magnetic separation of a target biological entity from a fluid sample, said system comprising:

at least one device according to any one of A1-A16;

a plurality of magnetic beads each functionalized to bind to the target biological entity, thereby being effective to capture and separate the target biological entity from the fluid sample.

B2. The system according to B1 further comprising an aggregation agent configured to group together an aggregate of a plurality of the target biological entities prior to the capture and separation of the target biological entity from the fluid sample.

B3. The system according to B2, wherein said aggregation agent is selected from the group consisting of an antibody, a protein, dextran, polyvinylpyrollidone, polyoxyethylene, fibrinogen, immunoglobulin IgM and IgG, calcium chloride, and combinations thereof.

B4. The system according to B2, wherein the target biological entity are red blood cells and the aggregation agent is an antibody that binds to red blood cells non-specifically, irrespective of blood type.

B5. The system according to B2, wherein the aggregation agent is an antibody that binds to a surface marker of red blood cells.

B6. The system according to B5, wherein the surface marker of the red blood cell is selected from the group consisting of CD235a and TER119.

B7. The system according to B2, wherein the plurality of magnetic beads and the aggregation agent are contained in a vessel comprising a tube or other suitable container for containing the fluid sample during operation of the device.

B8. The system according to B2, wherein the plurality of magnetic beads and the aggregation agent are provided together in a storage buffer.

B9. The system according to B2, wherein the plurality of magnetic beads are conjugated to the aggregation agent prior to adding the fluid sample.

B10. The system according to B2, wherein the plurality of magnetic beads and the aggregation agent are dried directly in a collection container prior to adding the fluid sample.

B11. The system according to B10, wherein the collection container is a vessel comprising a tube or other suitable container for containing the fluid sample during operation of the device.

B12. The system according to B1, wherein the target biological entity is selected from the group consisting of white blood cells, contaminants, waste products, and excess reagents contained in the fluid sample.

B13. The system according to B1 further comprising a collection component for collecting a supernatant produced after capture and separation of the target biological entity from the fluid sample.

B14. The system according to B13, wherein the collection component is a capillary tube configured to passively uptake the supernatant.

B15. The system according to B13, wherein the fluid sample is a blood sample, the target biological entity comprises red blood cells, and the supernatant comprises plasma.

C1. A method for separating a target biological entity from a fluid sample, said method comprising the steps of:

providing a device according to any one of A1-A16;

combining the fluid sample with a plurality of magnetic beads functionalized to bind to the target biological entity, wherein the combining is performed in a vessel comprising a tube or other suitable container for containing the fluid sample during operation of the device;

positioning the vessel containing the fluid sample and the functionalized magnetic beads between the two magnets of the magnetic separation chamber of the device; and operating the device in a manner sufficient to capture the target biological entity on the functionalized magnetic beads, thereby yielding a supernatant free of or substantially free of said target biological entity.

C2. The method according to C1, wherein the operating step comprises running the actuator to enable the magnetic separation chamber to function to capture the target biological entity with the functionalized magnetic beads and concentrate them proximate to just one of the two magnets, thereby separating the target biological entity from the fluid sample.

C3. The method according to C2, wherein running the actuator comprises moving the magnetic separation chamber laterally in a side-to-side motion with respect to the fluid sample for a sufficient number of strokes to homogenously distribute the functionalized magnetic beads among the target biological entity and concentrate them proximate to just one of the two magnets, thereby separating the target biological entity from the fluid sample.

C4. The method according to C3, wherein the number of strokes is not greater than 100 strokes, not greater than 50 strokes, not greater than 40 strokes, not greater than 30 strokes, not greater than 20 strokes, or not greater than 10 strokes.

C5. The method according to C3, wherein the sufficient number of strokes is completed within not more than 180 seconds, not more than 150 seconds, not more than 120 seconds, not more than 90 seconds, not more than 60 seconds, or not more than 30 seconds.

C6. The method according to C1 further comprising collecting the supernatant from the vessel.

C7. The method according to C6, wherein the collecting is performed using a capillary tube.

C8. The method according to C1 further comprising collecting and analyzing the supernatant and/or the captured target biological entity using one or more diagnostic tool or technique of interest.

C9. The method according to C1, wherein the method does not involve a centrifugation step to separate the target biological entity from the fluid sample.

C10. The method according to C1, wherein the magnetic beads are conjugated to an aggregation agent prior to the combining step, and wherein said aggregation agent is configured to group together an aggregate of a plurality of the target biological entities prior to the capture and separation of the target biological entity from the fluid sample.

C11. The method according to C10, wherein said aggregation agent is selected from the group consisting of an antibody, a protein, dextran, polyvinylpyrollidone, polyoxyethylene, fibrinogen, immunoglobulin IgM and IgG, calcium chloride, and combinations thereof.

C12. The method according to C10, wherein the target biological entity are red blood cells and the aggregation agent is an antibody that binds to red blood cells non-specifically, irrespective of blood type.

C13. The method according to C10, wherein the aggregation agent is an antibody that binds to a surface marker of red blood cells.

C14. The method according to C13, wherein the surface marker of the red blood cell is selected from the group consisting of CD235a and TER119.

C15. The method according to C10, wherein the plurality of magnetic beads and the aggregation agent are contained in a vessel comprising a tube or other suitable container for containing the fluid sample during operation of the device.

C16. The method according to C10, wherein the plurality of magnetic beads and the aggregation agent are provided together in a storage buffer.

C17. The method according to C10, wherein the plurality of magnetic beads are conjugated to the aggregation agent prior to adding the fluid sample.

C18. The method according to C10, wherein the plurality of magnetic beads and the aggregation agent are dried directly in a collection container prior to adding the fluid sample.

C19. The method according to C18, wherein the collection container is a vessel comprising a tube or other suitable container for containing the fluid sample during operation of the device.

C20. The method according to C1, wherein the target biological entity is selected from the group consisting of white blood cells, contaminants, waste products, and excess reagents contained in the fluid sample.

C21. The method according to C1 further comprising a collection component for collecting a supernatant produced after capture and separation of the target biological entity from the fluid sample.

C22. The method according to C21, wherein the collection component is a capillary tube configured to passively uptake the supernatant.

C23. The method according to C21, wherein the fluid sample is a blood sample, the target biological entity comprises red blood cells, and the supernatant comprises plasma.

Second Set of Examples of Embodiments of the Present Disclosure

Sleeve Device

A1. A device for use in magnetic separation of a target biological entity from a fluid sample, said device comprising:
a magnetic separation chamber configured to receive a fluid sample for magnetic separation, wherein said magnetic separation chamber comprises at least two magnets mounted on the surface or in the wall of the magnetic separation chamber,
a force provider configured to move the magnetic separation chamber in a side-to-side motion to mix and/or magnetize the fluid sample.

A2. The device according to A1, wherein the force provider is an actuator or a movable hand.

A3. The device according to A1, wherein the force provider is an actuator and the two magnets are mounted on opposing sidewalls a sufficient distance from one another so as to prevent interference between the magnetic field of each magnet,
wherein the magnetic separation chamber is configured to receive and maintain the fluid sample at a position between the two magnets during operation of the device, and
wherein the actuator is functionally coupled to the magnetic separation chamber, said actuator comprising a linear actuator configured to move the magnetic separation chamber laterally in a side-to-side motion so as to keep the two magnets in line with the fluid sample during operation of the actuator.

A4. The device according to A1, wherein the at least two magnets are fixed or movable along the wall of the magnetic separation chamber.

A5. The device according to A1, wherein the magnetic separation chamber further comprises at least two channels along the sidewall of the chamber to allow the at least two magnets movable in order to mix and magnetize the sample.

A6. The device according to A1, wherein the at least two channels are linear channels, curved channels, symmetric channels, cylindrical shaped, or tube shaped.

A7. The device according to A1, wherein the force provider is a manual force provider or an automatic force provider.

A8. The device according to A1, wherein the fluid sample further comprises at least an aggregation agent configured to group together an aggregate of a plurality of the target biological entities.

A9. The device according to A1, wherein the device further comprises a collection component for collecting a supernatant produced after capture and separation of the target biological entity from the fluid sample, and wherein the collection component is cap comprising capillary tube.

A10. The device according to A1, said magnetic separation chamber comprising a durable plastic material or any other non-magnetic material.

A11. The device according to A1, wherein the at least two magnets are ball magnets.

A12. The device according to A11, wherein the ball magnets are $3/16$ inch ball magnets.

A13. The device according to A11, wherein the magnetic separation chamber is in a form of a sleeve and comprises a substantially central channel for loading a vessel containing the fluid sample therein.

A14. The device according to A13, wherein the substantially central channel has a circumference suitable for a standard blood collection tube.

A15. The device according to A14, wherein the substantially central channel has a circumference of approximately 10 mm and a depth of approximately 70-75 mm.

A16. The device according to A13, wherein the sleeve is configured to contain a vessel comprising a 3 mL tube.

A17. The device according to A13, wherein the vessel can contain a volume of fluid sample selected from the group consisting of up to 200 uL, up to 500 uL, up to 1 mL, up to 1.5 mL, up to 2.0 mL, up to 2.5 mL, up to 3.0 mL, and up to 5.0 mL.

A18. The device according to A13, wherein the vessels can contain a volume of fluid sample of 200 uL or greater.

A19. The device according to A13, wherein the sleeve is made with 3D printed plastic or any durable plastic or non-magnetic material.

A20. The device according to A13, wherein the sleeve is made with injection molding techniques.

A21. The device according to A13, wherein the sleeve comprises dimensions approximating those of a 10 mL blood tube, said dimensions comprising approximately 16 mm in circumference and 100 mm in length for the depth of the substantially central channel, wherein total size of the sleeve can alternatively scale up or down according to these dimensions accordingly.

A22. The device according to A21, wherein the size of the sleeve can be scaled up at least by approximately 1.5 times.

B1 A method for separating a target biological entity from a fluid sample, said method comprising the steps of:
providing a device according to any one of A1-A22;
combining the fluid sample with a plurality of magnetic beads functionalized to bind to the target biological entity, wherein the combining is performed in a vessel comprising a tube or other suitable container for containing the fluid sample during operation of the device;

positioning the vessel containing the fluid sample and the functionalized magnetic beads between the two magnets of the magnetic separation chamber of the device; and operating the device in a manner sufficient to capture the target biological entity on the functionalized magnetic beads, thereby yielding a supernatant free of or substantially free of said target biological entity.

B2. The method according to B1 further comprising collecting the supernatant from the vessel.

B3. The method according to B1 further comprising collecting and analyzing the supernatant and/or the captured target biological entity using one or more diagnostic tool or technique of interest.

B4. The method according to B1, wherein the method does not involve a centrifugation step to separate the target biological entity from the fluid sample.

B5. The method according to B1, wherein the magnetic beads are conjugated to an aggregation agent prior to the combining step, and wherein said aggregation agent is configured to group together an aggregate of a plurality of the target biological entities prior to the capture and separation of the target biological entity from the fluid sample.

B6. The method according to B5, wherein said aggregation agent is selected from the group consisting of an antibody, a protein, dextran, polyvinylpyrollidone, polyoxyethylene, fibrinogen, immunoglobulin IgM and IgG, calcium chloride, and combinations thereof.

B7. The method according to B5, wherein the target biological entity are red blood cells and the aggregation agent is an antibody that binds to red blood cells non-specifically, irrespective of blood type.

B8. The method according to B5, wherein the aggregation agent is an antibody that binds to a surface marker of red blood cells.

B9. The method according to B8, wherein the surface marker of the red blood cell is selected from the group consisting of CD235a and TER119.

B10. The method according to B5, wherein the plurality of magnetic beads and the aggregation agent are contained in a vessel comprising a tube or other suitable container for containing the fluid sample during operation of the device.

B11. The method according to B5, wherein the plurality of magnetic beads and the aggregation agent are provided together in a storage buffer.

B12. The method according to B5, wherein the plurality of magnetic beads are conjugated to the aggregation agent prior to adding the fluid sample.

B13. The method according to B5, wherein the plurality of magnetic beads and the aggregation agent are dried directly in a collection container prior to adding the fluid sample.

B14. The method according to B13, wherein the collection container is a vessel comprising a tube or other suitable container for containing the fluid sample during operation of the device.

B15. The method according to B1, wherein the target biological entity is selected from the group consisting of white blood cells, contaminants, waste products, and excess reagents contained in the fluid sample.

B16. The method according to B1 further comprising a collection component for collecting a supernatant produced after capture and separation of the target biological entity from the fluid sample.

B17. The method according to B16, wherein the collection component is a capillary tube configured to passively uptake the supernatant.

B18. The method according to B16, wherein the fluid sample is a blood sample, the target biological entity comprises red blood cells, and the supernatant comprises plasma.

Illustrative embodiments of the processes, methods, and products of the present disclosure are described herein. It should be understood, however, that the description herein of the specific embodiments is not intended to limit the present disclosure to the particular forms disclosed but, on the contrary, the intention is to cover all modifications equivalents and alternatives falling within the spirit and scope of the invention by the appended claims. Thus, although the present invention has been described for the purpose of illustration, it is understood that such detail is solely for that purpose and variations can be made by those skilled in the art without departing from the spirit and scope of the invention which is defined by the following claims.

What is claimed is:

1. A device for use in magnetic separation of a target biological entity from a fluid sample, said device comprising:
    a magnetic separation chamber configured to receive a fluid sample for magnetic separation, wherein said magnetic separation chamber comprises two magnets mounted on opposing sidewalls a sufficient distance from one another so as to prevent interference between the magnetic field of each magnet, and wherein the magnetic separation chamber is configured to receive and maintain the fluid sample at a position between the two magnets during operation of the device; and
    an actuator functionally coupled to the magnetic separation chamber, wherein said actuator comprises a linear actuator configured to move the magnetic separation chamber laterally in a side-to-side motion so as to keep the two magnets in line with the fluid sample during operation of the actuator.

2. The device according to claim 1, wherein the magnetic separation chamber is configured to receive a fluid sample having a volume of up to 200 microliters.

3. The device according to claim 1, wherein the magnetic separation chamber is configured to receive a vessel comprising a tube or other suitable container containing the fluid sample.

4. The device according to claim 1, wherein the magnets are circular magnets or neodymium magnets.

5. The device according to claim 1 further comprising a housing unit configured to house the magnetic separation chamber and the actuator.

6. The device according to claim 5, wherein the housing unit comprises a base portion and a top cover portion, wherein the base portion is configured to hold the magnetic separation chamber and the actuator, and wherein the top cover portion is configured to fit over and cover the base portion and its contents.

7. The device according to claim 6, wherein the top cover portion further comprises an opening for inserting the fluid sample into a position between the two magnets of the magnetic separation chamber.

8. The device according to claim 5, wherein the housing unit is configured to further house onboard electronics components effective to operate the actuator and to enable automation of the device.

9. The device according to claim 8, wherein the onboard electronics components comprise at least one component selected from the group consisting of a microcontroller, a transistor, and a power input jack.

10. The device according to claim 9, wherein the power input jack is suitable for use with a standard 12 volt, 0.5 ampere wall power supply.

11. The device according to claim 1, wherein the device is in a form of a portable benchtop device.

12. The device according to claim 11, wherein the portable benchtop device has dimensions not greater than 4 centimeters in height, 5 centimeters in width, and 8 centimeters in length.

13. The device according to claim 1, wherein the device is in a form suitable for use for point-of-need diagnostics of the fluid sample.

14. A system for use in magnetic separation of a target biological entity from a fluid sample, said system comprising:
at least one device according to claim 1;
a plurality of magnetic beads each functionalized to bind to the target biological entity, thereby being effective to capture and separate the target biological entity from the fluid sample.

15. The system according to claim 14 further comprising an aggregation agent configured to group together an aggregate of a plurality of the target biological entities prior to the capture and separation of the target biological entity from the fluid sample.

16. The system according to claim 15, wherein said aggregation agent is selected from the group consisting of an antibody, a protein, dextran, polyvinylpyrrolidone, polyoxyethylene, fibrinogen, immunoglobulin IgM and IgG, calcium chloride, and combinations thereof.

17. The system according to claim 15, wherein the target biological entity are red blood cells and the aggregation agent is an antibody that binds to red blood cells non-specifically, irrespective of blood type.

18. The system according to claim 15, wherein the aggregation agent is an antibody that binds to a surface marker of red blood cells.

19. The system according to claim 18, wherein the surface marker of the red blood cell is selected from the group consisting of CD235a and TER119.

20. The system according to claim 15, wherein the plurality of magnetic beads and the aggregation agent are:
(a) contained in a vessel comprising a tube or other suitable container for containing the fluid sample during operation of the device;
(b) provided together in a storage buffer;
(c) conjugated to one another prior to adding the fluid sample; or
(d) dried directly in a collection container prior to adding the fluid sample.

21. The system according to claim 20, wherein the collection container is a vessel comprising a tube or other suitable container for containing the fluid sample during operation of the device.

22. The system according to claim 14, wherein the target biological entity is selected from the group consisting of white blood cells, contaminants, waste products, and excess reagents contained in the fluid sample.

23. The system according to claim 14 further comprising a collection component for collecting a supernatant produced after capture and separation of the target biological entity from the fluid sample.

24. The system according to claim 23, wherein the collection component is a capillary tube configured to passively uptake the supernatant.

25. The system according to claim 23, wherein the fluid sample is a blood sample, the target biological entity comprises red blood cells, and the supernatant comprises plasma.

26. A method for separating a target biological entity from a fluid sample, said method comprising the steps of:
providing a device according to claim 1;
combining the fluid sample with a plurality of magnetic beads functionalized to bind to the target biological entity, wherein the combining is performed in a vessel comprising a tube or other suitable container for containing the fluid sample during operation of the device;
positioning the vessel containing the fluid sample and the functionalized magnetic beads between the two magnets of the magnetic separation chamber of the device; and
operating the device in a manner sufficient to capture the target biological entity on the functionalized magnetic beads, thereby yielding a supernatant free of or substantially free of said target biological entity.

* * * * *